(12) United States Patent
Seubsai et al.

(10) Patent No.: US 8,829,211 B2
(45) Date of Patent: Sep. 9, 2014

(54) DIRECT CONVERSION OF OLEFIN TO OLEFIN OXIDE BY MOLECULAR OXYGEN

(75) Inventors: Anusorn Seubsai, Bangkok (TH); Selim Senkan, Los Angeles, CA (US); Yoshihiko Ohishi, Osaka (JP); Carlos Gustavo Knapp Bjeren, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/979,393

(22) PCT Filed: Jan. 18, 2012

(86) PCT No.: PCT/US2012/021656
§ 371 (c)(1),
(2), (4) Date: Jul. 12, 2013

(87) PCT Pub. No.: WO2012/102918
PCT Pub. Date: Aug. 2, 2012

(65) Prior Publication Data
US 2013/0296586 A1 Nov. 7, 2013

Related U.S. Application Data

(60) Provisional application No. 61/435,523, filed on Jan. 24, 2011, provisional application No. 61/550,840, filed on Oct. 24, 2011.

(51) Int. Cl.
C07D 301/06 (2006.01)
C07D 301/08 (2006.01)
B01J 27/057 (2006.01)
B01J 27/13 (2006.01)

(52) U.S. Cl.
CPC .............. B01J 27/13 (2013.01); C07D 301/08 (2013.01); B01J 27/0576 (2013.01)
USPC ......................................... 549/533; 549/532

(58) Field of Classification Search
USPC ......................................... 549/533, 523, 532
See application file for complete search history.

(56) References Cited

U.S. PATENT DOCUMENTS 2,680,752 A 6/1954 Voge et al.
3,076,032 A 1/1963 Riemenschneider
(Continued)

FOREIGN PATENT DOCUMENTS

CN 1376538 A 10/2002
CN 101927195 A 12/2010
(Continued)

OTHER PUBLICATIONS

John R. Monnier, "The direct epoxidation of higher olefins using molecular oxygen", Applied Catalysis A: General, vol. 221, 2001, pp. 73-91.

(Continued)

Primary Examiner — T. Victor Oh
(74) Attorney, Agent, or Firm — Sughrue Mion, PLLC

(57) ABSTRACT

The present invention relates to a direct conversion of olefin to olefin oxide, which are important and versatile intermediates used in the production of a large variety of valuable consumer products such as polyurethane foams, polymers, alkylene glycol, cosmetics, food emulsifiers and as fumigants and insecticides. More specifically, the present invention provides a process for producing an olefin oxide which comprises reacting an olefin with oxygen in the presence of a halogen compound additive and a catalyst comprising copper, ruthenium or both thereof.

11 Claims, 29 Drawing Sheets

(56) References Cited

U.S. PATENT DOCUMENTS

| | | | |
|---|---|---|---|
| 3,122,586 | A | 2/1964 | Berndt et al. |
| 6,362,349 | B1* | 3/2002 | Kuperman et al. ............ 549/533 |
| 6,765,101 | B1 | 7/2004 | Bhasin et al. |
| 2003/0187283 | A1 | 10/2003 | Jansen et al. |
| 2003/0191328 | A1 | 10/2003 | Jansen et al. |
| 2005/0239643 | A1 | 10/2005 | Benderly et al. |
| 2010/0331571 | A1 | 12/2010 | Saito et al. |
| 2012/0283454 | A1 | 11/2012 | Senkan et al. |
| 2012/0283455 | A1 | 11/2012 | Senkan et al. |
| 2013/0281722 | A1* | 10/2013 | Ohishi et al. .................. 549/523 |

FOREIGN PATENT DOCUMENTS

| | | | |
|---|---|---|---|
| JP | 2002-371074 | A | 12/2002 |
| JP | 2002371074 | * | 12/2002 |
| WO | 0187867 | A1 | 11/2001 |
| WO | 2009/134839 | A1 | 11/2009 |
| WO | 2011075459 | A1 | 6/2011 |

OTHER PUBLICATIONS

Owain P.H. Vaughan, et al., "Copper as a selective catalyst for the epoxidation of propene", Journal of Catalysis, vol. 236, 2005, pp. 401-404.

Zhaoxia Song, et al., "Gas-phase epoxidation of propylene through radicals generated by silica-supported molybdenum oxide", Applied Catalysis A: General, vol. 316, 2007, pp. 142-151.

Toshio Hayashi, et al., "Formation of Propylene Oxide by the Gas-Phase Reaction of Propane and Propene Mixture with Oxygen", Ind. Eng. Chem. Res., vol. 34, 1995, pp. 2298-2304.

Toshio Hayashi, et al., "Selective Vapor-Phase Epoxidation of Propylene over Au/TiO$_2$ Catalysts in the Presence of Oxygen and Hydrogen", Journal of Catalysis, vol. 178, 1998, pp. 566-575.

B.S. Uphade, et al., "Effect of physical mixing of CsCl with Au/Ti—MCM-41 on the gas-phase epoxidation of propene using H$_2$ and O$_2$: Drastic depression of H$_2$ comsumption", Applied Catalysis A: General, vol. 190, 2000, pp. 43-50.

Anil K. Sinha, et al., "A Three-Dimensional Mesoporous Titanosilicate Support for Gold Nanoparticles: Vapor-Phase Epoxidation of Propene with High Conversion", Angew. Chem. Int. Ed., vol. 43, 2004, pp. 1546-1548.

Kazuhisa Murata and Yoshimichi Kiyozumi, "Oxidation of propene by molecular oxygen over Ti-modified silicalite catalysts", Chem. Commun., 2001, pp. 1356-1357.

Kazuhisa Murata, et al., "Direct vapor phase oxidation of propylene by molecular oxygen over MCM-41 or MCM-22 based catalysts", Catalysis Communications, vol. 4, 2003, pp. 385-391.

T.A. Nijhuis, et al., "The direct epoxidation of propene by molten salts", Applied Catalysis A: General, vol. 196, 2000, pp. 217-224.

Selim Senkan, et al., "High-Throughput Testing of Heterogeneous Catalyst Libraries Using Array Microreactors and Mass Spectrometry", Angew. Chem. Int. Ed., vol. 38, No. 18, 1999, pp. 2794-2799.

International Preliminary Report on Patentability and Written Opinion issued Aug. 8, 2013 in International Application No. PCT/US2012/021656 to Sumitomo Chemical Co., Ltd., et al.

International Search Report of PCT/US2012/021656 dated May 1, 2012.

Seubsai et al., "New Catalytic Materials for the Direct Epoxidation of Propylene by Molecular Oxygen," ChemCatChem, vol. 3, 2011, pp. 174-179.

European Patent Office, "Communication with Extended Search Report," issued in connection with European Patent Application No. 12739958.2, dated Jun. 4, 2014.

State Intellectual Property Office, P.R. China, "First Office Action," issued in connection with Chinese Patent Application No. 201280006281.0 dated Jun. 13, 2014.

Sinfelt, J.H. et al., "Nature of Ruthenium-Copper Catalysts," Journal of Catalysts, vol. 42, No. 2, 1976, pp. 227-237.

Bailey, A.J. et al., "Oxo Complexes of Ruthenium with N, N-donors as Oxidation Catalysts for Alkenes, Alkanes and Alcohols, and Their Osmium Analogues," Journal of the Chemical Society, Dalton Transactions, vol. 1995, No. 21, pp. 3537-3542.

* cited by examiner (a)

(b)

(a)

(b)

DIRECT CONVERSION OF OLEFIN TO OLEFIN OXIDE BY MOLECULAR OXYGEN

CROSS-REFERENCE TO RELATED PATENT APPLICATIONS

This application claims priority to and the benefit of U.S. Provisional Application Nos. 61/435,523, filed Jan. 24, 2011, and 61/550,840, filed Oct. 24, 2011, incorporated by reference herein in its entirety.

BACKGROUND

Olefin oxides, such as propylene oxide, are important and versatile intermediates used in the production of a large variety of valuable consumer products such as polyurethane foams, polymers, alkylene glycol, cosmetics, food emulsifiers and as fumigants and insecticides.

Previous research on olefin epoxidation involved the use of Ag-based catalysts (*Appl. Catal. A. Gen.* 2001, 221, 73.), as well as silica supported Cu (*J. Catal.* 2005, 236, 401), various metal oxides (*Appl. Catal. A. Gen.* 2007, 316, 142), Au-based catalysts with $H_2$ as a co-reactant (*Ind. & Eng. Chem. Res.* 1995, 34, 2298, *J. Catal.* 1998, 178, 566; *Appl. Catal. A. Gen.* 2000, 190, 43; *Angew. Chem. Int. Ed.* 2004, 43, 1546), titania based catalysts that deactivated quickly (*Chem. Commun.* 2001, 1356; *Catal. Commun.* 2003, 4, 385), molten salts of metal nitrates (*Appl. Catal. A. Gen.* 2000, 196, 217), the use of $O_3$ (*Appl. Catal. A. Gen.* 2000, 196, 217) and nitrous oxide (*Ind. & Eng. Chem. Res.* 1995, 34, 2298) as reactants. Although these developments are scientifically interesting, they have serious drawbacks, such as low PO selectivities and/or low propylene conversions, short catalyst lifetimes, the use of higher pressures or the use of costly co-reactants (*Appl. Catal. A. Gen.* 2007, 316, 142).

As to a process for producing olefin oxides, olefin epoxidation in the presence of a metal-based catalyst has been proposed. For example, US2003/0191328 mentions a process for the epoxidation of hydrocarbon with oxygen in the presence of a mixture containing at least two metals from the specific metal group on a support having a specific BET surface area. JP2002-371074 mentions a process for producing an oxirane compound which process uses a metal oxide catalyst containing at least one metal selected from the metals belonging to the Group III to XVI of the periodic table.

SUMMARY OF INVENTION

The present invention provides:

[1] A process for producing an olefin oxide which comprises reacting an olefin with oxygen in the presence of a halogen compound additive and a catalyst comprising copper, ruthenium or both thereof.
[2] The process according to [1], wherein the catalyst comprises a copper oxide, a ruthenium oxide or both of thereof.
[3] The process according to [1], wherein the catalyst comprises a copper oxide and a ruthenium oxide.
[4] The process according to [1], wherein the catalyst further comprises an alkaline metal or alkaline earth metal component.
[5] The process according to [1], wherein the catalyst further comprises a component deriving from one selected from the group consisting of P, S, B, Mn, Ge, Tl, In, Ir, La, Ce, Bi, Re, Cr, Fe, Mo, W, Se, Sb, V, Ni, Co, Sn, Nb, Os, lanthanoid, and Te.
[6] The process according to [5], wherein the component is a tellulium component.
[7] The process according to [1], wherein copper, ruthenium or both thereof are supported on a support.
[8] The process according to [1], wherein the support is a porous support.
[9] The process according to [1], wherein the halogen compound additive is a saturated or unsaturated halogen compound.
[10] The process according to [9], wherein the saturated or unsaturated halogen compound is a fluorinated hydrocarbon, a chlorinated hydrocarbon, a bromo hydrocarbon or an iodo hydrocarbon.
[11] The process according to [10], wherein hydrocarbon is a C1-C4 alkane or alkene.
[12] The process according to [1], wherein the amount of the halogen compound additive is 0.1 to 1000 ppm of entire reaction gas.
[13] A catalyst for producing an olefin oxide which comprises an olefin with oxygen in the presence of a halogen compound additive and a catalyst comprising copper, ruthenium or both thereof.
[14] The catalyst according to [13], which comprises a copper oxide, a ruthenium oxide or both of thereof.
[15] The catalyst according to [13], which comprises a copper oxide and a ruthenium oxide.
[16] The catalyst according to [13], which further comprises an alkaline metal or alkaline earth metal component.
[17] The catalyst according to [13], which further comprises a component deriving from one selected from the group consisting of P, S, B, Mn, Ge, Tl, In, Ir, La, Ce, Bi, Re, Cr, Fe, Mo, W, Se, Sb, V, Ni, Co, Sn, Nb, Os, lanthanoid, and Te.
[18] The catalyst according to [17], wherein the component is a tellulium component.
[19] The process according to [13], wherein copper, ruthenium or both thereof are supported on a support.
[20] The catalyst according to [13], wherein the support is a porous support.
[21] The catalyst according to [13], wherein the halogen compound additive is a saturated or unsaturated halogen compound.
[22] The catalyst according to [21], wherein the saturated or unsaturated halogen compound is a fluorinated hydrocarbon, a chlorinated hydrocarbon, a bromo hydrocarbon or an iodo hydrocarbon.
[23] The catalyst according to [22], wherein hydrocarbon is a C1-C4 alkane or alkene.
[24] Use of a catalyst for producing an olefin oxide which comprises an olefin with oxygen in the presence of a halogen compound additive and a catalyst comprising copper, ruthenium or both thereof.

DESCRIPTION OF THE INVENTION

Figure 1:
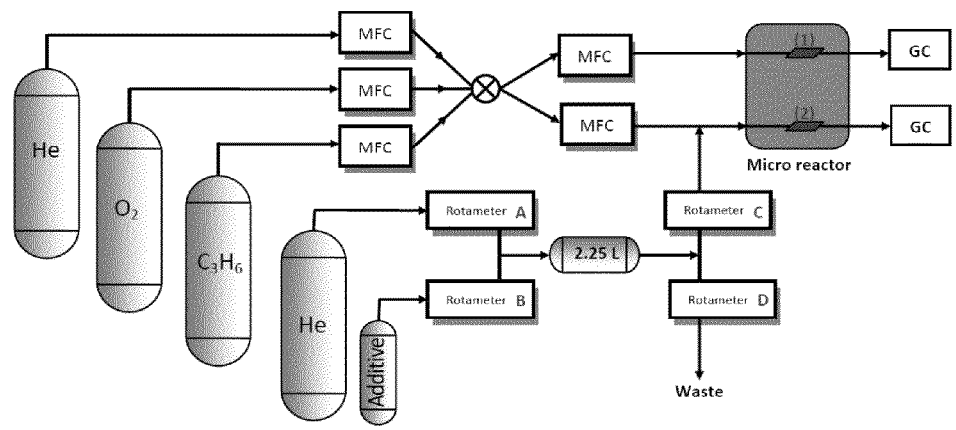
FIG. 1 is a schematic of the system of Experimental Set-up No. 1.

The Influence of Halogen Compound Additives on Olefin Epoxidation Catalysts.

The initial Ru—Cu—NaCl/SiO$_2$ catalysts discovered for olefin epoxidation, e.g., propylene epoxidation, using oxygen have exhibited delayed deactivation problems at long reaction times. We also explored co-feeding halogen compound additives, e.g., chlorinated hydrocarbon additives, to determine their effects on olefin epoxidation, specifically propylene epoxidation selectivity and rates, for a variety of lead catalysts under both propylene-rich (excess propylene) and propylene-lean (excess oxygen) conditions.

We performed simultaneous (i.e., parallel) time-on-stream experiments with and without chlorinated additives for the Ru—Cu—NaCl/SiO$_2$ (main discovery) as well as new leads Ru—Mn—NaCl/SiO$_2$, Sn—Cu—NaCl/SiO$_2$ and Sb—Cu—NaCl/SiO$_2$ catalysts. Additionally, we can also use alternative catalysts, for example, Ru—Cu/SiO$_2$, Cu-M-Na/SiO$_2$ (M=Ru, Sn, Sb, Mn, Bi, Cr, Re, Co, Ni, Os, lanthanoid, Ge, W and Tl), Ru-M'-Na/SiO$_2$ (M'=Mn, Bi, Sb), Ru—Cu—Na-M"/SiO$_2$ (M"=Mn, Ge, Tl, In, Ir, La, Ce, Bi, Re, Cr, Fe, Mo, W, Se, Sb, V, Ni, Sn, Nb, Co), Ru—Cu—Na—P/SiO$_2$, Ru—Cu—Na—S/SiO$_2$, Ru—Cu—Na—B/SiO$_2$, Cu—Te/SiO$_2$, Cu—Te—Ru/SiO$_2$, Ru—Te/SiO$_2$ and Cu—Ru—Te—Na/SiO$_2$.

In these catalysts as mentioned above, each metal generally forms a metal oxide comprised of the metal and an oxygen atom(s). The alternative catalysts also include what comprise two or three metals which are contained together in each of the catalysts as mentioned above and other supports instead of SiO$_2$; what comprise two or three metals as mentioned above and an alkaline metal excepting Na, and optionally a support such as a porous support including SiO$_2$; what comprise two or three metals as mentioned above and an alkaline earth metal, and optionally a support such as SiO$_2$; and what comprise two or three metals as mentioned above. Herein, the alkaline metal other than Na includes K, Rb and Cs. The alkaline earth metal includes Ca, Mg, Sr and Ba. The alkaline metal or the alkaline earth metal disclosed herein may form a salt with a halogen ion such as Cl$^-$, F$^-$, Br$^-$ or I$^-$. If the catalysts disclosed herein are supported on a porous support, they are obtained, for example, by impregnating a porous support with a solution containing metal ions of two or three metals as mentioned above, and optionally an alkaline metal or alkaline earth metal ion or other components such as halogen ions or P-, S-, or B-containing ion to prepare a composition, followed by calcining the composition. The impregnation can be conducted in a solvent such as water or polar organic solvents. The calcination can be conducted at a temperature of 200 to 800° C. Each process can be conducted selecting a suitable condition by way of a known manner.

The support may be a porous support, and may be a non-porous support. The porous support has pores capable of supporting the copper oxide, and/or the ruthenium oxide. The porous support comprises preferably Al$_2$O$_3$, SiO$_2$, TiO$_2$, or ZrO$_2$, more preferably SiO$_2$. Examples of the porous support comprising SiO$_2$ include mesoporous silica. Such a porous support may also comprise zeolite. Examples of the non-porous support include a non-porous support comprising SiO$_2$ such as CAB-O-SIL (registered trade mark). The support may be in a form of powder or may be shaped to a desired structure.

The catalyst comprises one or more kinds of copper oxide. The copper oxide is usually composed of copper and oxygen. Examples of the copper oxide include Cu$_2$O and CuO, preferably CuO.

The catalyst comprises one or more kinds of ruthenium oxide. The ruthenium oxide is usually composed of ruthenium and oxygen. Examples of the ruthenium oxide include Ru$_2$O$_4$, Ru$_2$O$_5$, Ru$_3$O$_5$, Ru$_3$O$_6$, RuO$_4$, and RuO$_2$, preferably RuO$_2$.

The catalyst may comprise one or more kinds of manganese oxide. The manganese oxide is usually composed of manganese and oxygen. Examples of the manganese oxide include MnO, MnO$_2$, Mn$_2$O$_3$ and Mn$_3$O, preferably Mn$_2$O$_3$ and Mn$_3$O$_4$.

The catalyst may comprise one or more kinds of germanium oxide. The germanium oxide is usually composed of germanium and oxygen. Examples of germanium oxide include GeO and GeO$_2$, preferably GeO$_2$.

The catalyst may comprise one or more kinds of thallium oxide. The thallium oxide is usually composed of thallium and oxygen. Examples of the thallium oxide include Tl$_2$O, Tl$_2$O$_3$ and Tl$_4$O$_3$, preferably Tl$_4$O$_3$.

The catalyst may comprise one or more kinds of indium oxide. The indium oxide is usually composed of indium and oxygen. Examples of the indium oxide include In$_2$O$_3$.

The catalyst may comprise one or more kinds of iridium oxide. The iridium oxide is usually composed of iridium and oxygen. Examples of the iridium oxide include IrO$_2$.

The catalyst may comprise one or more kinds of iron oxide. The iron oxide is usually composed of iron and oxygen. Examples of the iron oxide include FeO, Fe$_2$O$_3$ and Fe$_3$O$_4$, preferably Fe$_2$O$_3$.

The catalyst may comprise one or more kinds of molybdenum oxide. The molybdenum oxide is usually composed of molybdenum and oxygen. Examples of the molybdenum oxide include MoO$_2$ and MoO$_3$.

The catalyst may comprise one or more kinds of selenium oxide. The selenium oxide is usually composed of selenium and oxygen. Examples of the selenium oxide include SeO$_2$ and SeO$_3$, preferably SeO$_3$.

The catalyst may comprise one or more kinds of vanadium oxide. The vanadium oxide is usually composed of vanadium and oxygen. Examples of the vanadium oxide include VO, VO$_2$, V$_2$O$_3$, V$_2$O$_5$, and V$_6$O$_{13}$, preferably V$_2$O$_5$.

The catalyst may comprise one or more kinds of niobium oxide. The niobium oxide is usually composed of niobium and oxygen. Examples of the niobium oxide include NbO, $NbO_2$ and $Nb_2O_5$.

The catalyst may comprise one or more kinds of tellurium oxide. The tellurium oxide is usually composed of tellurium and oxygen. Examples of the tellurium oxide include TeO, $TeO_2$, $TeO_3$ and $Te_2O_5$.

The catalyst may comprise one or more kinds of tellurium salt. The tellurium salt is usually composed of tellurium ion such as $Te^{2+}$, $Te^{4+}$, $Te^{6+}$ and $Te^{2-}$ and an anion such as $F^-$, $Cl^-$, $Br^-$, $I^-$, $NO_3^-$ and $CO_3^{2-}$.

The catalyst may comprise one or more kinds of bismuth oxide. The bismuth oxide is usually composed of bismuth and oxygen. Examples of the bismuth oxide include BiO, $BiO_2$, $Bi_2O$ and $Bi_2O_3$, preferably $Bi_2O_3$.

The catalyst may comprise one or more kinds of rhenium oxide. The rhenium oxide is usually composed of rhenium and oxygen. Examples of the rhenium oxide include $ReO_2$, $ReO_3$ and $Re_2O_7$, preferably $ReO_2$ or $ReO_3$.

The catalyst may comprise one or more kinds of chromium oxide. The chromium oxide is usually composed of chromium and oxygen. Examples of chromium oxide include $CrO_3$, and $Cr_2O_3$, preferably $Cr_2O_3$.

The catalyst may comprise one or more kinds of tungsten oxide. The tungsten oxide is usually composed of tungsten and oxygen. Examples of the tungsten oxide include $W_3O$, $W_{17}O_{47}$, $W_5O_{14}$, $WO_x$, $WO_2$ and $WO_3$, preferably $WO_2$ and $WO_3$.

The catalyst may comprise one or more kinds of antimony oxide. The antimony oxide is usually composed of antimony and oxygen. Examples of the antimony oxide include $SbO_2$, $Sb_2O_3$, $Sb_2O_4$ and $Sb_2O_5$, preferably $SbO_2$ or $Sb_2O_3$.

The catalyst may comprise one or more kinds of nickel oxide. The nickel oxide is usually composed of nickel and oxygen. Examples of the nickel oxide include NiO.

The catalyst may comprise one or more kinds of cobalt oxide. The cobalt oxide is usually composed of cobalt and oxygen. Examples of the cobalt oxide include CoO, $Co_3O_4$ and $Co_2O_3$, preferably $Co_3O_4$.

The catalyst may comprise one or more kinds of tin oxide. The tin oxide is usually composed of tin and oxygen. Examples of the tin oxide include $SnO_2$, SnO, $Sn_2O_3$ and $Sn_3O_4$, preferably $SnO_2$ and SnO.

The catalyst may comprise one or more kinds of osmium oxide. The osmium oxide is usually composed of osmium and oxygen. Examples of osmium oxide include $OsO_2$ and $OsO_4$, preferably $OsO_2$.

The catalyst may comprise one or more kinds of lanthanoid oxide. The lanthanoid oxide is usually composed of lanthanoid and oxygen. Examples of the lanthanoid oxide include lanthanum oxide, cerium oxide, praseodymium oxide, neodymium oxide, promethium oxide, samarium oxide, europium oxide, gadolinium oxide, terbium oxide, dysprosium oxide, holmium oxide, erbium oxide, thulium oxide, ytterbium oxide and lutetium oxide, preferably lanthanum oxide, cerium oxide, samarium oxide and gadolinium oxide, more preferably LaO, $La_2O_3$, $Ce_2O_3$, $CeO_2$, $Sm_2O_3$ and $Gd_2O_3$, still more preferably $CeO_2$.

The catalyst comprises one or more kinds of the alkaline metal or alkaline earth metal component. The alkaline metal or alkaline earth metal component may be an alkaline metal-containing compound, an alkaline earth metal-containing compound, an alkaline metal ion or an alkaline earth metal ion. Examples of the alkaline metal-containing compound include compounds containing an alkaline metal such as Na, K, Rb and Cs. Examples of the alkaline earth metal-containing compound include compounds containing an alkaline metal earth metal such as Ca, Mg, Sr and Ba. Examples of the alkaline metal ion include $Na^+$, $K^+$, $Rb^+$ and $Cs^+$. Examples of the alkaline earth metal ion include such as $Ca^{2+}$, $Mg^{2+}$, $Sr^{2+}$ and $Ba^{2+}$. The alkaline metal compound may be an alkaline metal oxide. Examples of the alkaline metal oxide include $Na_2O$, $Na_2O_2$, $K_2O$, $K_2O_2$, $Rb_2O$, $Rb_2O_2$, $Cs_2O$, and $Cs_2O_2$. The alkaline earth metal component may be alkaline earth metal oxide. Examples of the alkaline earth metal oxide include CaO, $CaO_2$, MgO, $MgO_2$, SrO, $SrO_2$, BaO and $BaO_2$. The alkaline metal or alkaline earth metal component is preferably an alkaline metal-containing compound, more preferably a sodium-containing compound.

Production of the catalyst is not restricted to a specific process, examples of which include the conventional methods, for example, impregnation method, precipitation method, deposition precipitation, chemical vapor deposition, mechano-chemical method, solid state reaction method, and the like, preferably impregnation method.

When the metal components are supported on a porous support in the catalyst, the catalyst can be obtained by impregnating a porous support with a solution containing metal ions to prepare a composition, followed by calcining the composition. The support can be in a form of powder, or shaped to a desired structure as necessary.

The solution containing the above-mentioned ions can be prepared by dissolving a metal salt in a solvent.

At least one of the metal salts for the solvent contains preferably a halogen ion, more preferably a chloride ion.

Examples of the solvent for the solution include water, alcohols such as methanol or ethanol, and ethers. As a source of water, ion-exchanged water is usually used. The amount of water, alcohols or ethers as the solvent is not limited, preferably 0.01 to 2000 parts by weight per part by weight of copper in the mixture. If the catalyst contains a support, the amount of water, alcohols or ethers as the solvent is preferably 0.01 to 500 parts by weight per part by weight of support in the mixture, more preferably 0.1 to 100 parts by weight per part by weight of support in the mixture.

The mixture solution composed of metal salts described above or support is preferably aged with stirring at a temperature of 5° C. to 100° C., more preferably 10° C. to 50° C. The mixture solution can be used as is, but is preferably aged for some time. Aging time is preferably in the range from 0.5 to 48 hours, more preferably 1 to 25 hours.

The composition as prepared by the impregnation is usually dried, and the drying method thereof is not limited. For example, evaporation to dryness, spray drying, drum drying, flash drying and the like. The composition as prepared by the impregnation is preferably dried at a temperature of 10° C. to 250° C., more preferably 40° C. to 200° C., before calcining the composition. Drying may be performed under an atmosphere of air or also under an inert gas atmosphere (for example, Ar, $N_2$, He) at standard pressure or reduced pressure. A drying time is preferably in the range from 0.5 to 24 hours. After drying, the composition can be shaped to a desired structure as necessary.

Calcining the composition is not limited, but preferably may be performed under a gas atmosphere containing oxygen and/or inert gas such as nitrogen, helium and argon. Examples of such a gas include air, an oxygen gas, nitrous oxide, and other oxidizing gases. The gas may be used after being mixed at an appropriate ratio with a diluting gas such as nitrogen, helium, argon, and water vapor. An optimal temperature is typically 250 to 800° C., preferably 400 to 600° C. The calcining time is preferably in the range from 0.5 hour to 24 hours.

The catalyst can be used as powder, but it is usual to shape it into desired structures such as spheres, pellets, cylinders, rings, hollow cylinders or stars. The catalyst can be shaped by a known procedure such as extrusion, ram extrusion, tableting. The calcination is normally performed after shaping into the desired structures, but it can also be performed before shaping them. Halogen compound additives, in general had a similar and beneficial effect on olefin oxide selectivities for all of the catalytic systems and under all conditions investigated. That is, halogen compound additives either increased olefin oxide selectivities or prevented their decrease with time-on-stream. The halogen compound additive is preferably a saturated or unsaturated organohalogen compound capable of existing as a gas under the conditions of temperature and pressure in the reaction system of olefin epoxidation. More specifically, examples of the saturated or unsaturated halogen compound include, for example, an organic fluorine compound such as fluorinated hydrocarbon; an organic chlorine compound such as chlorinated hydrocarbon; an organic bromine compound such as bromo hydrocarbon; and an organic iodine compound such as iodo hydrocarbon. Each of the hydrocarbons is preferably an alkane or alkene, more preferably a C1-C4 alkane or alkene. More preferably, an organic chlorine compound is used, and the compound includes, for example, chlorinated hydrocarbon. The chlorinated hydrocarbon includes alkyl chlorides or allyl chlorides, e.g. chloromethane, chloroethane, 1,2-dichloroethane, vinyl chloride, tetrachloroethylene, trichloroethylene, 1-chloropropane, 1,2-dichloropropane, 1,3-dichloropropane, 1,2,3-trichloropropane and allyl chloride. The optimum amount of the halogen compound to be supplied varies depending on factors such as a concentration of olefin, a concentration of oxygen, an amount of the catalysts described above, but is usually from 0.1 ppm to 1000 ppm, and preferably from 1 ppm to 500 ppm, of the entire reaction gas.

We completed a manuscript reporting the effects of chlorinated hydrocarbons in propylene epoxidation for the above mentioned catalysts (*Chem. Cat. Chem.*, 2011, 3, 1751).

In Table 1 the list of chlorinated hydrocarbons used as well as their forms and concentrations in the feed are shown. Since the physical properties of the CHCs are different, several experimental systems were developed to introduce the desired levels of various CHCs to the propylene/oxygen/helium feed gas.

Figure 2:
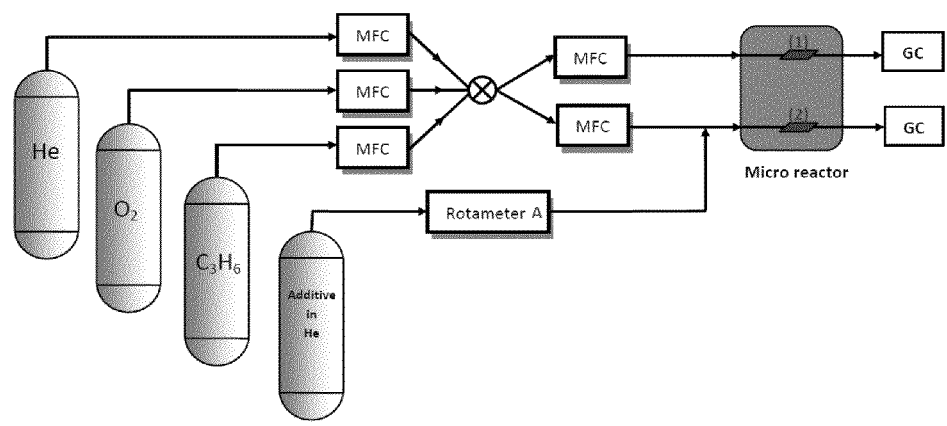
FIG. 2 is a schematic of the system of Experimental Set-up No. 2.
Figure 3:
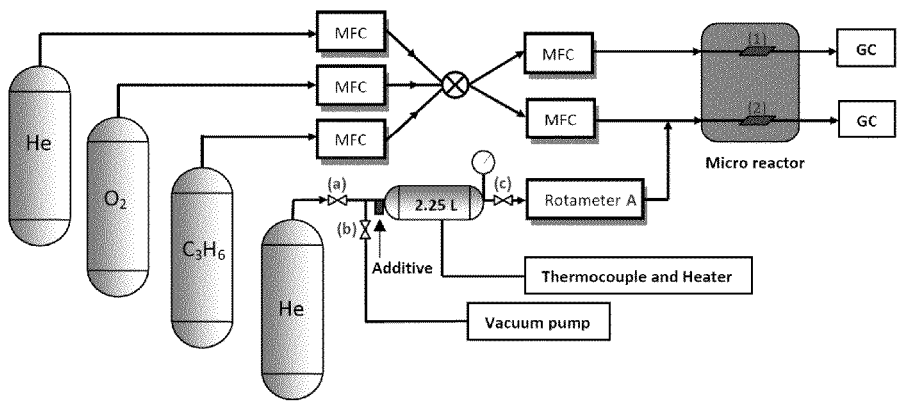
FIG. 3 is a schematic of the system of Experimental Set-up No. 3.

Sketches of the experimental systems used are presented in FIGS. 1, 2, and 3. More specifically, FIG. 1 presents a Schematic system of the Experimental set-up no. 1: For the introduction of chloromethane and chloroethane [Typically, Rotameter A is set at 400 cc/min, B at 1 cc/min, C at 0.5 or 1.0 cc/min]. FIG. 2 presents Schematic system of the Experimental set-up no. 2: For the introduction of 1,2-dichloroethane [2,000 ppm balance with He (Matheson-Trigas company)]. FIG. 3 presents a Schematic system of the Experimental set-up no. 3: For the introduction of Ethyl dichloride (EtCl$_2$), 1-Chloropropane, 1,2-Dichloropropane, 1,3-Dichloropropane, 1,2,3-Trichloropropane, and Allyl Chloride.

The experimental systems can be adopted to other reactions which are conducted using the different materials disclosed herein. Virtually all experiments were performed under which the CHC additive was introduced on a continuous basis. However, a limited number of experiments with ethylene dichloride (EtCl$_2$) were also performed where the CHC is introduced intermittently.

TABLE 1

The details on the experiments of the addition of chloro-additives to the system of the lead catalysts

| Additive | Appearance | Boiling Point (° C.) | Density (mg/μL) | Temp. of the 2.25 L tank (° C.) | Set-up no. | Amount of additive (ppm) | |
|---|---|---|---|---|---|---|---|
| | | | | | | C$_3$H$_6$-Lean | C$_3$H$_6$-Rich |
| Chloromethane | Pressurized Liquid | — | — | — | 1 | 25 | 25 |
| Chloroethane | Pressurized Liquid | — | — | — | 1 | 25, 15* | 25 |
| 1,2-Dichloroethane | 2000 ppm in He | — | — | — | 2 | 100 | 150 |
| 1-Chloropropane | Liquid | 47 | 0.892 | 100 | 3 | 12 | 24 |
| 1,2-Dichloropropane | Liquid | 95 | 1.157 | 120 | 3 | 4.6 | — |
| 1,3-Dichloropropane | Liquid | 120 | 1.190 | 140 | 3 | 2.5 | — |
| 1,2,3-Trichloropropane | Liquid | 158 | 1.385 | 170 | 3 | 4.7 | — |
| Allyl Chloride | Liquid | 46 | 0.939 | 100 | 3 | 5.2 | — |

Testing condition: 250° C., using 5.0 mg of fresh catalysts, GHSV = 20,000 h$^{-1}$. [*17,000 h$^{-1}$ for Ru—Cu—NaCl]
C$_3$H$_6$-Lean: 1% of C$_3$H$_6$, 4% of O$_2$, and He balance
C$_3$H$_6$-Rich: 2.5% of C$_3$H$_6$, 1% of O$_2$, and He balance Next, the following explains a reaction of an olefin with oxygen in the presence of the catalyst as described above.

The olefin may have a linear or branched structure and contains usually 2 to 10, preferably 2 to 8 carbon atoms. The olefin may be a monoolefin or a diolefin. Examples of the monoolefin include ethylene, propylene, butene, pentene, hexane, heptene, octene, nonene, and decene. Examples of the diene include butadiene such as 1,3-butadiene or 1,2-butadiene. Examples of the olefin include preferably monoolefin, more preferably ethylene, propylene, butene, pentene, hexene, heptene and octene, still more preferably ethylene, propylene and butene, most preferably propylene.

The reaction is generally performed in the gas phase. In the reaction, the olefin and oxygen may be fed respectively in the form of a gas. Olefin and oxygen gases can be fed in the form of their mixed gas. Olefin and oxygen gases may be fed with diluent gases. Examples of diluent gases include nitrogen, methane, ethane, propane, carbon dioxide, or rare gases, such as argon and helium.

As the oxygen source, pure oxygen may be used, or a mixed gas containing a gas inactive to the reaction, such as air, may be used. The amount of oxygen used varies depending on the reaction type, the catalyst, the reaction temperature or the like. The amount of oxygen is typically 0.01 to 100 mol, and preferably 0.03 to 30 mol, and more preferably 0.05 to 10 mol, with respect to 1 mol of the olefin.

The reaction is performed at a temperature generally of 100 to 350° C., preferably of 120 to 330° C., more preferably of 170 to 310° C.

The reaction is usually carried out under reaction pressure in the range of reduced pressure to increased pressure. By carrying out the reaction under such a reaction pressure condition, the productivity and selectivity of olefin oxides can be improved. Reduced pressure means a pressure lower than atmospheric pressure. Increased pressure means a pressure higher than atmospheric pressure. The pressure is typically in the range of 0.01 to 3 MPa, and preferably in the range of 0.02 to 2 MPa, in the absolute pressure.

The gaseous hourly space velocity (Liters of gas at standard temperature and pressure passing over the one liter of packed catalyst per hour: GHSV) is generally in the range of from 100 Nl/(l·h) to 100000 Nl/(l·h), preferably 500 Nl/(l·h) to 50000 Nl/(l·h). The linear velocity is generally in the range of from 0.0001 m/s to 500 m/s, and preferably in the range of 0.001 m/s to 50 m/s.

The reaction may be carried out as a batch reaction or a continuous reaction, preferably as a continuous reaction for industrial application. The reaction of the present invention may be carried out by mixing an olefin and oxygen and then contacting the mixture with the catalyst under reduced pressure to the increased pressure.

The reactor type is not limited. Examples of the reactor type are fluid bed reactor, fixed bed reactor, moving bed reactor, and the like, preferably fixed bed reactor. In the case of using fixed bed reactor, single tube reactor or multi tube reactor can be employed. More than one reactor can be used. If the number of reactors is large, small reactors as for example microreactors, can be used, which can have multiple channels. Adiabatic type or heat exchange type may also be used.

In the present invention, the olefin oxide may have a linear or branched structure and contains usually 2 to 10, preferably 2 to 8 carbon atoms. The olefin oxide may have one carbon-carbon double bond when the diolefin is applied for the reaction. Examples of the olefin oxide having one carbon-carbon double bond include 3,4-epoxy-1-butene. Examples of the olefin oxides include preferably ethylene oxide, propylene oxide, butene oxide, pentene oxide, hexene oxide, heptene oxide and octene oxide, more preferably ethylene oxide, propylene oxide and butene oxide, still more preferably propylene oxide.

The olefin oxide as obtained can be collected by a method known in the art such as separation by distillation. The olefin oxide as obtained can be collected by absorption with a suitable solvent such as water and acetonitrile followed by conducting a method known in the art such as separation by distillation.

The operation of systems 1 and 2 are straightforward. For the case of liquid CHCs, the experimental system 3 was used in a manner described below:

1. Typical testing condition; Reactor temperature: 240° C., Feed gas composition: 1% of $C_3H_6$, 4% of $O_2$ and He balance [set the MFC of $C_3H_6$=20 cc/min, $O_2$=80 cc/min and He=1900 cc/min], GHSV of catalyst (1) and (2) is 20,000 $h^{-1}$ (100 cc/min per bank), using 5.0 mg of Ru—Cu—NaCl/$SiO_2$ catalyst placed on (1) as reference data without the chlorinated additive and (2) for the results with the chlorinated additive.
2. When the temperature reaches at 240° C., start flowing the feed gases for catalyst (1) and (2).
3. Use GC to monitor catalysts (1) and (2) until the onset of deactivation of the catalysts (i.e. PO selectivity starts decreasing).
4. Prepare the chlorinated hydrocarbon addition into the system:
   4.1. Set the outlet pressure gauge of He at 80 psi.
   4.2. Control the temperature of the 2.25 L tank at 100° C. using heater and a thermocouple.
   4.3. Flush and vacuum out the 2.25 L tank with He several times.
   4.4. Fill up the tank with He to atmospheric pressure (1 atm). The pressure gauge of the tank reads 0 relative pressure.
   4.5. Inject a predetermined amount of liquid chlorinated hydrocarbon (e.g. 10 micro-liter) using a GC syringe through a septum into the tank. Under the prevailing conditions, the chlorinated hydrocarbons evaporate due to their high volatility.
   4.6. Pressurize the tank with He until 80 psi, which also mixes the contents.
   4.7. Wait additional 5 minutes to ensure mixing in the tank and the establishment of a uniform mixture. For example, if 10 microliters of dichloroethane is injected, the 2.25 L tank would contain 0.02678% by volume (267.8 ppm) of $EtCl_2$ by using the ideal gas law.
5. To co-feed the chlorinated hydrocarbon mixture to the system
   5.1. Close valve A and open valve B and C.
   5.2. Adjust the MFC of He from 1900 cc/min to 1322 cc/min, set the MFC for the chlorinated additive mixture to 29 cc/min, and also adjust the MFC of the feeding gases for catalyst (2) from 100 cc/min to 71 cc/min, so that the gas composition of $C_3H_6$ and $O_2$, and GSHV remain the same for catalyst (2).
   5.3. Monitor the catalysts (1), (2), and also an empty site for both reactor systems.
   5.4. In the example given above, the $EtCl_2$ concentration in the feed gas would be 77 ppm.
   5.5. The amount of gas in the 2.25 L tank is adequate to perform continuous experiments for about 20-100 min, depending on the concentration of CHC fed to the reactor bank. Consequently, the long-time experiments were performed by quickly replenishing the gas mixture in the tank. The temporary cut-off of the CHC additives had no observable effect on the results. However, this problem could easily be remedied by using 2 parallel tanks and by switching the flows back-and-forth as needed.
6. Repeat Steps 2-5 as needed.

The catalyst was evaluated by using a micro-reactor. The catalyst (5.0 mg) was placed in a well of a reactor as mentioned in *Angew. Chem. Int. Ed.* 38 (1999) 2794, equipped with array microreactors, wells along each reactor channel and a passivated 200 micron ID capillary sampling probe within the reactor channel. Gas sampling was accomplished by withdrawing reactor exit gases using the passivated 200 micron ID capillary sampling probe. The data analysis was conducted by an on-line Micro-Gas Chromatograph (Varian, CP-4900) equipped with a thermal conductivity detector (TCD), PoraPLOT U (10M) and Molecular sieve 13× (10M).

The detected products were propylene oxide (PO), acetone (AT), $CO_2$, CO, and propanal (PaL) and acrolein (AC).

Propylene conversions ($X_{PR}$) were determined from the following:

$$X_{PR} = \{[PO+AC+AT+PaL+CO_2/3]_{out}[C_3H_6]_{in} \times 100\%;$$
and; PO selectivities ($S_{PO}$) were then calculated using the following expression:

$$S_{PO} = \{[PO]/[PO+AC+AT+PaL+CO_2/3] \times 100\%$$

Catalyst Preparation i) Ru—Cu—Na/$SiO_2$

Amorphous silica powder (1.9 g; $SiO_2$, Japan Aerosil, 380 $m^2$/g) was added to an aqueous solution mixture containing 0.55 g of $(NH_4)_2RuCl_6$ (Alfa), 0.30 g of $Cu(NO_3)_2$ (Wako), 0.10 g of NaCl (Wako) and 40 g of $H_2O$. The obtained mixture was stirred for 24 hours in air, at 25° C. The resulting material was then heated at 100° C. until dried, and calcined at 500° C. for 12 hours in air to obtain the catalyst having the following composition.

The molar ratio of Ru/Cu/Na: 1.3/1/1.4.

The total amount of Ru, Cu and Na: 14.3 parts by weight relative to 100 parts by weight of $SiO_2$.

ii) Ru—Cu—Na—Te/$SiO_2$

Amorphous silica powder (3.9 g; $SiO_2$, Japan Aerosil, 380 $m^2$/g) was added to an aqueous solution mixture containing 0.43 g of $(NH_4)_2RuCl_6$ (Alfa), 0.60 g of $Cu(NO_3)_2$ (Wako), 0.20 g of NaCl (Wako), 0.05 g of $TeO_2$ (Wako) and 40 g of $H_2O$. The obtained mixture was stirred for 24 hours in air, at room temperature. The resulting material was then heated at 100° C. until dried, and calcined at 500° C. for 12 hours in air to obtain the metal oxide composition having the following composition.

The molar ratio of Ru/Cu/Na/Te: 0.5/1/1.4/0.1.

The total amount of Ru, Cu, Na and Te: 10.4 parts by weight relative to 100 parts by weight of $SiO_2$.

iii) Other Catalysts

Ru—Mn—NaCl/$SiO_2$, Sn—Cu—NaCl/$SiO_2$ and Sb—Cu—NaCl/$SiO_2$ catalysts were prepared in the same condition described above.

The weight ratio of Ru/Mn/Na, Sn/Cu/Na, and Sb/Cu/Na: 4/2/1.

The total amount of metal component: 14.3 parts by weight relative to 100 parts by weight of $SiO_2$.

Figure 4:
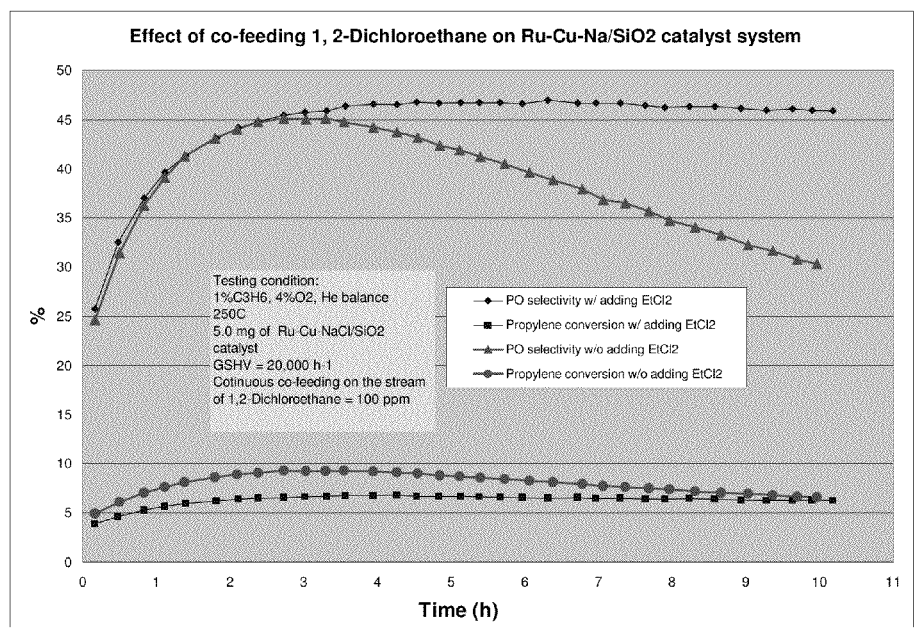
FIG. 4 is a graph showing the effects of feeding 1,2-dichloroethane on Ru—Cu—NaCl/$SiO_2$ catalyst.

Initial Experiments with the $RuO_2$/$CuO_x$/NaCl Supported on $SiO_2$ Catalysts FIG. 4 shows a typical time-on-stream experiment of Ru—Cu—NaCl/$SiO_2$ catalyst without addition of an additive (triangles). Clearly, the PO selectivity increased to the optimum at around 2-3 hour test, and then it slightly decreased with time. The continuous presence of 100 ppm $EtCl_2$ in the feed had a remarkable effect of maintaining PO selectivity at 45% indefinitely (rhombuses). However, $EtCl_2$ decreased propylene conversion slightly early on (squares), but its effect at long reaction times was not much different.

Figure 5:
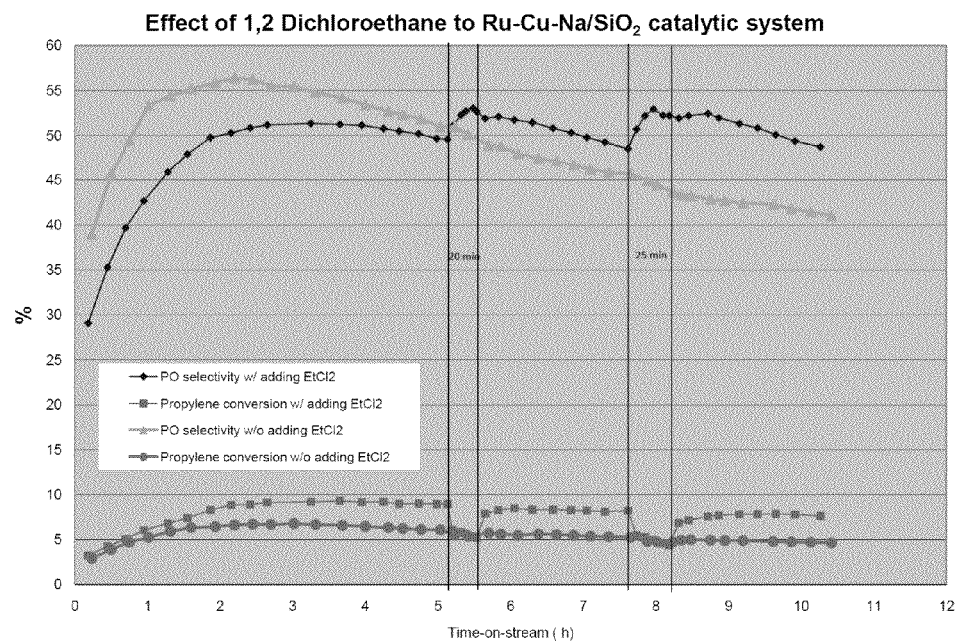
FIG. 5 is a graph showing the effects of intermittently feeding 1,2-dichloroethane on Ru—Cu—NaCl/$SiO_2$ catalyst.

Another experiment with $EtCl_2$ introduced intermittently has also been performed and the results are shown in FIG. 5. In this case, 77 ppm $EtCl_2$ was added to the feed stream for 20-25 minutes when the PO selectivity started to decrease. As seen in FIG. 5, the PO selectivity was brought back to normal with $EtCl_2$ addition, concomitant with a decrease in propylene conversion from 8% to 5%. When $EtCl_2$ was switched off propylene conversion immediately recovered while PO selectivity started exhibiting its normal slow decreasing trend.

$RuO_2$—CuO/$SiO_2$ with Co-Feeding Organic Halides

Figure 6:
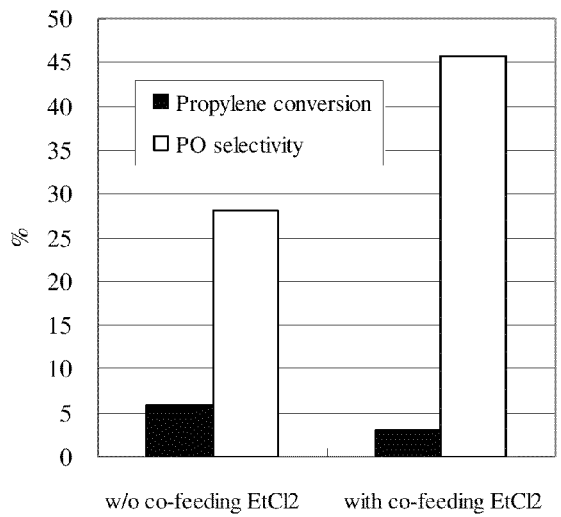
FIG. 6 is a graph showing the effects on PO selectivity of feeding 1,2-dichloroethane on Ru–Cu—NaCl/$SiO_2$ catalyst.
Figure 7:
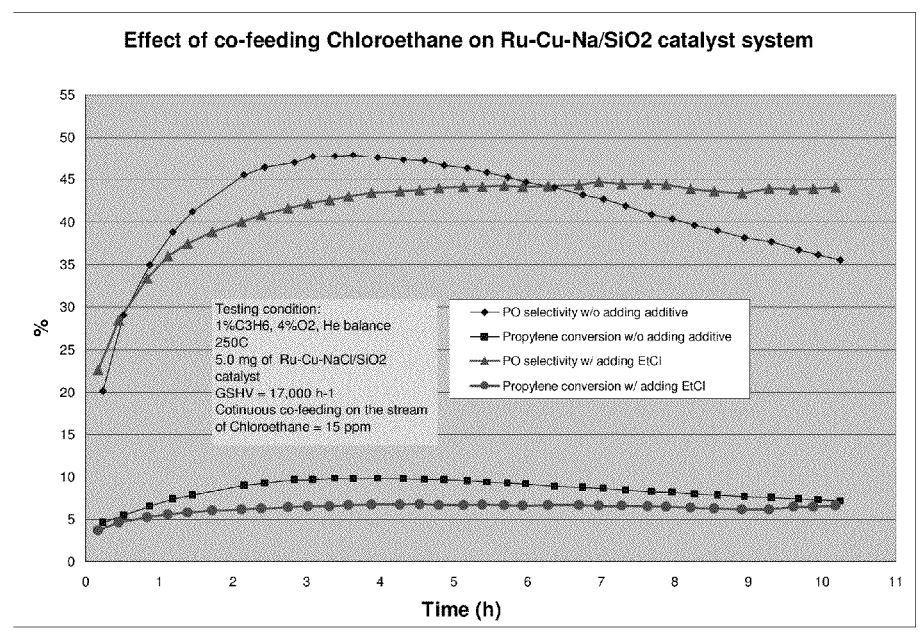
FIG. 7 to FIG. 37 are graphs showing the effects of continuously feeding 1,2-dichloroethane on Ru—Cu—NaCl/SiO$_2$ catalyst under different testing conditions, but all under propylene-lean conditions (i.e., 1% C$_3$H$_6$, 4% O$_2$, balance helium)
Figure 8:
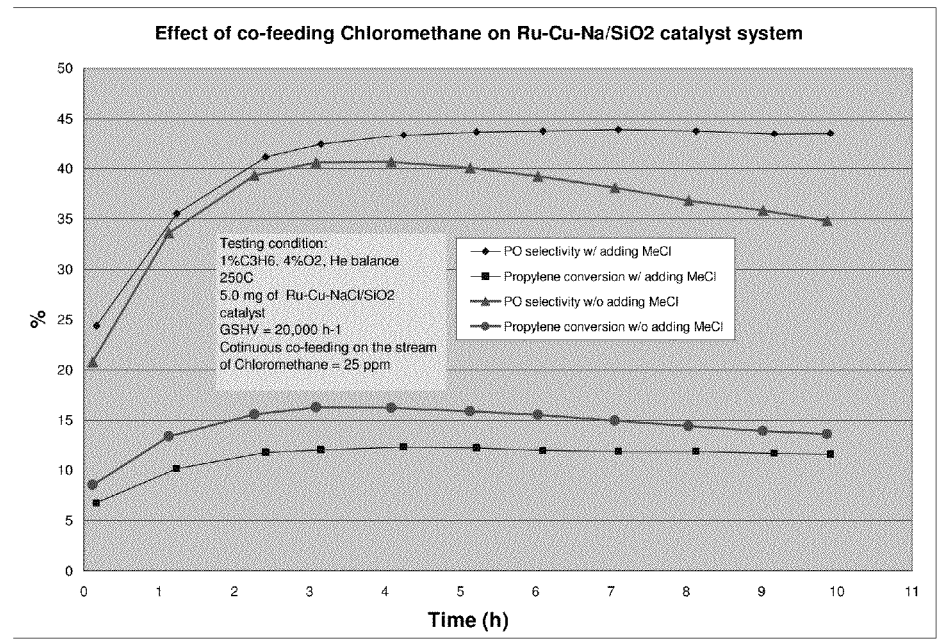
Figure 9:
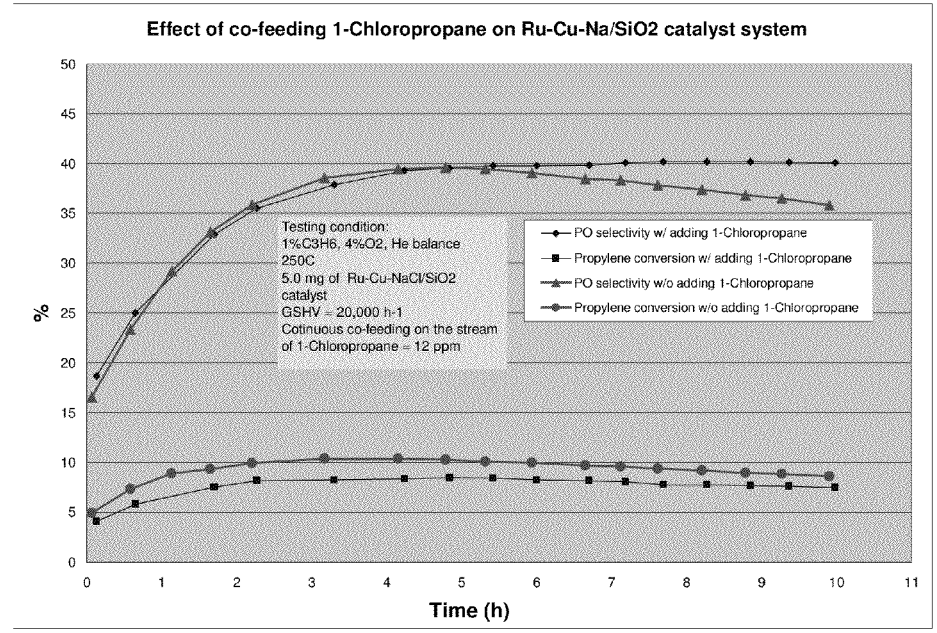
Figure 10:
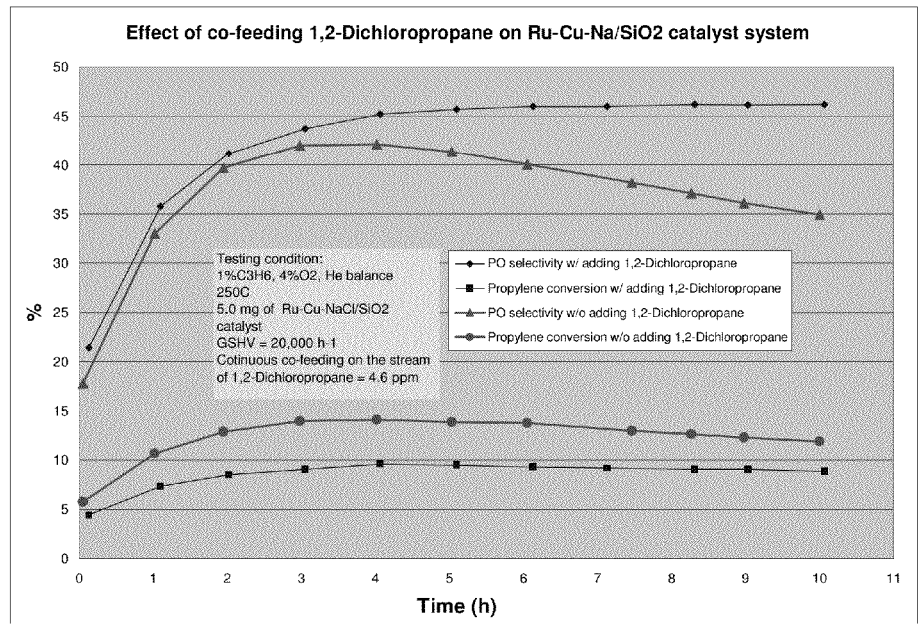
Figure 11:
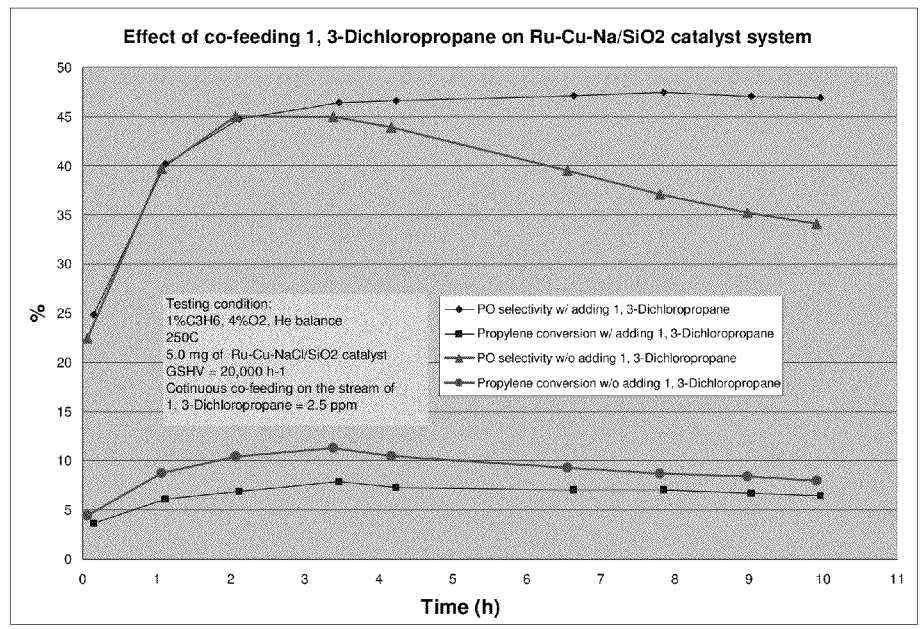
Figure 12:
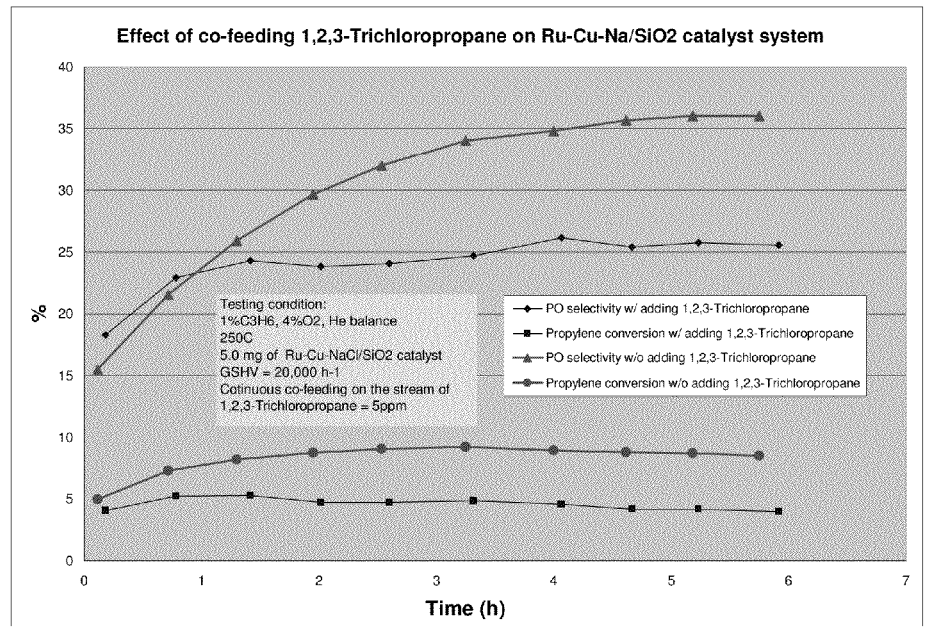
Figure 13:
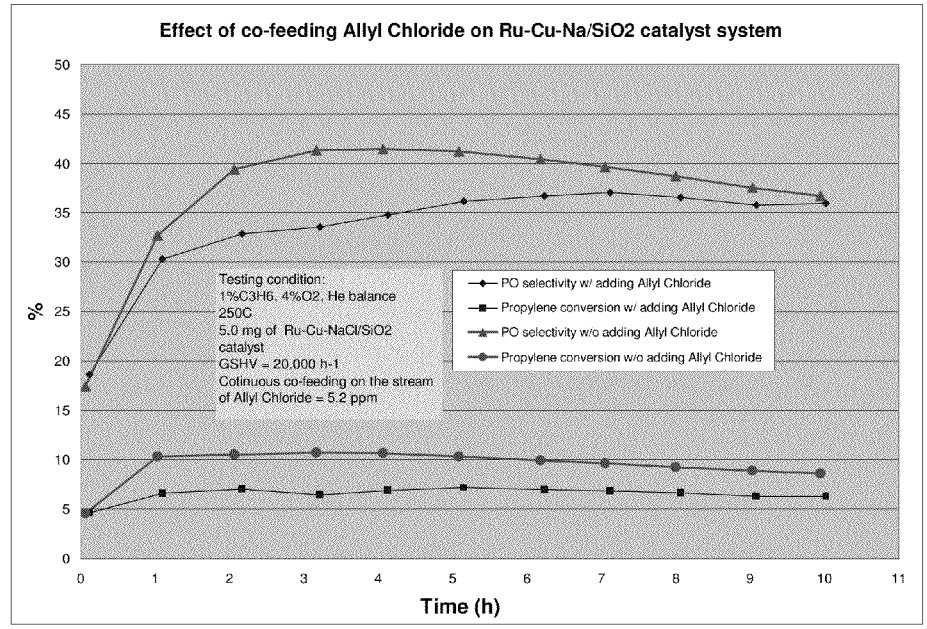
Figure 14:
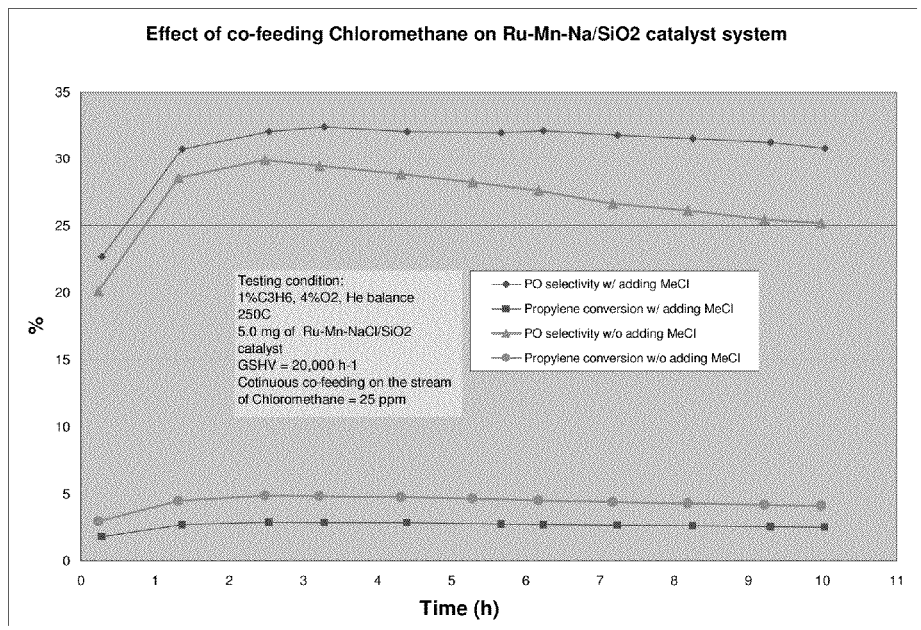
Figure 15:
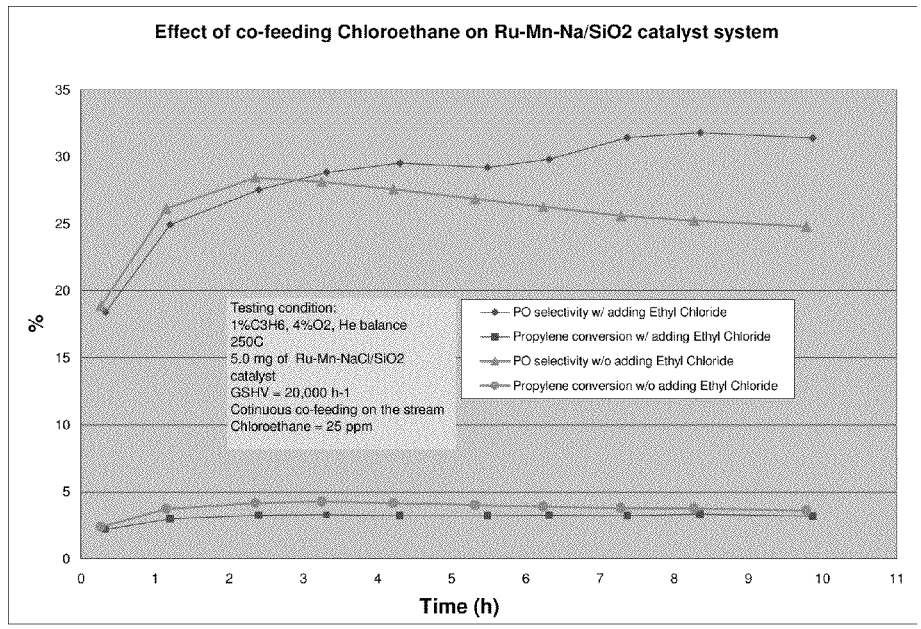
Figure 16:
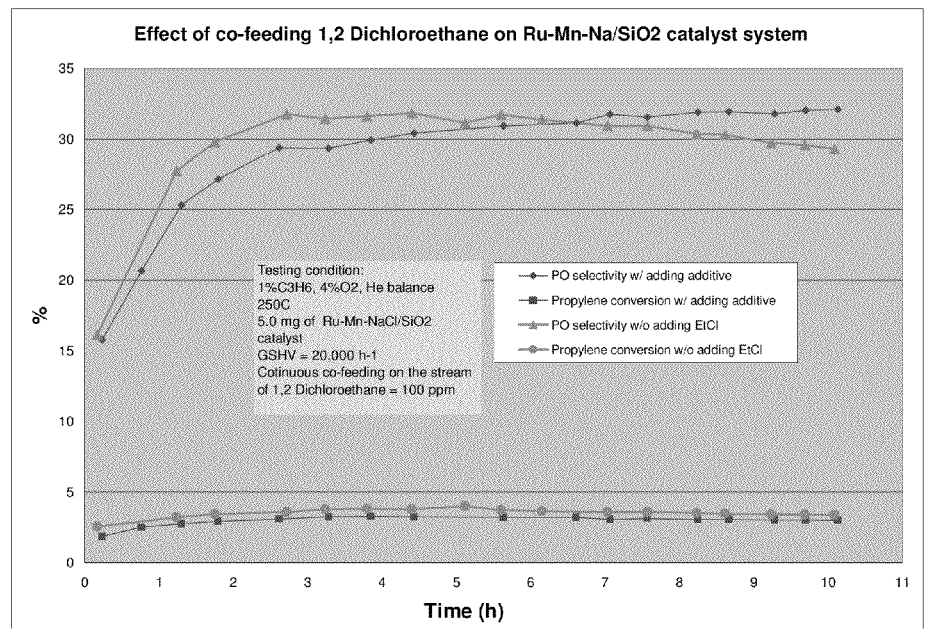
Figure 17:
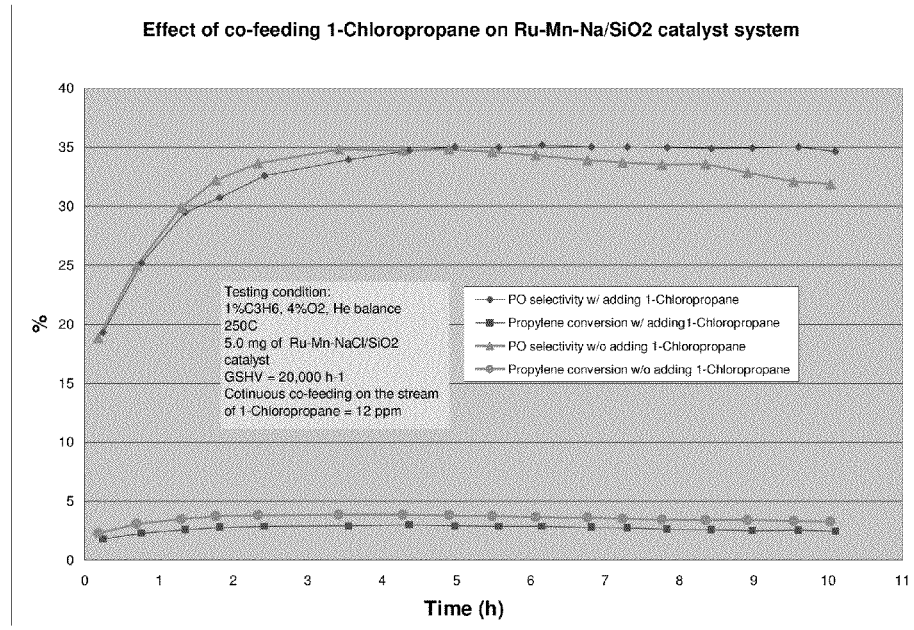
Figure 18:
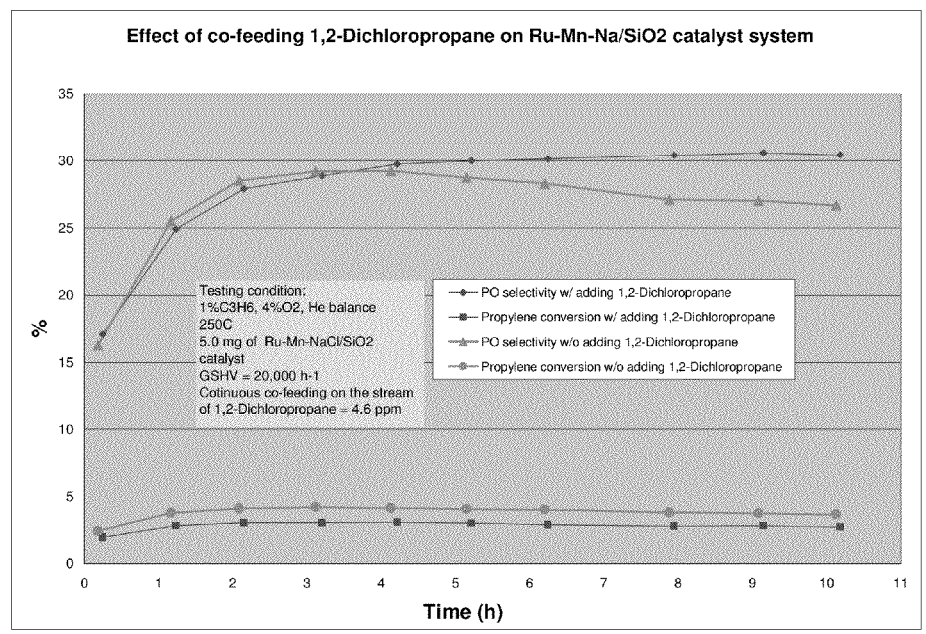
Figure 19:
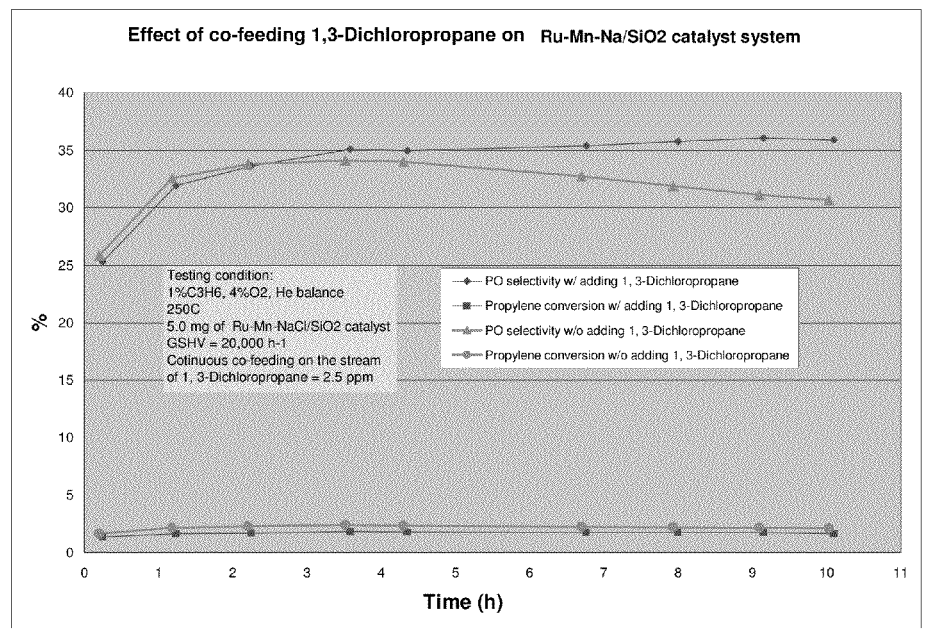
Figure 20:
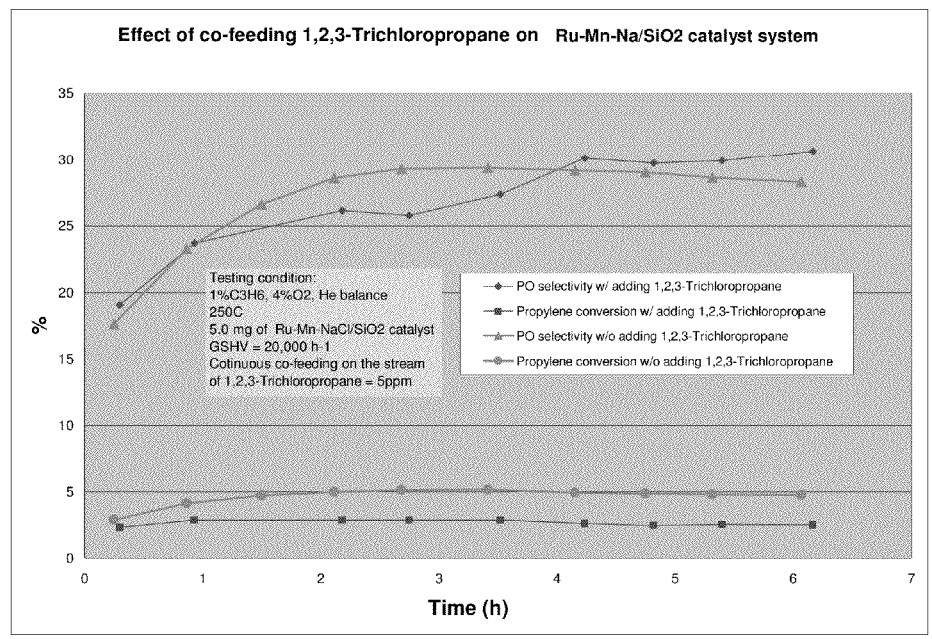
Figure 21:
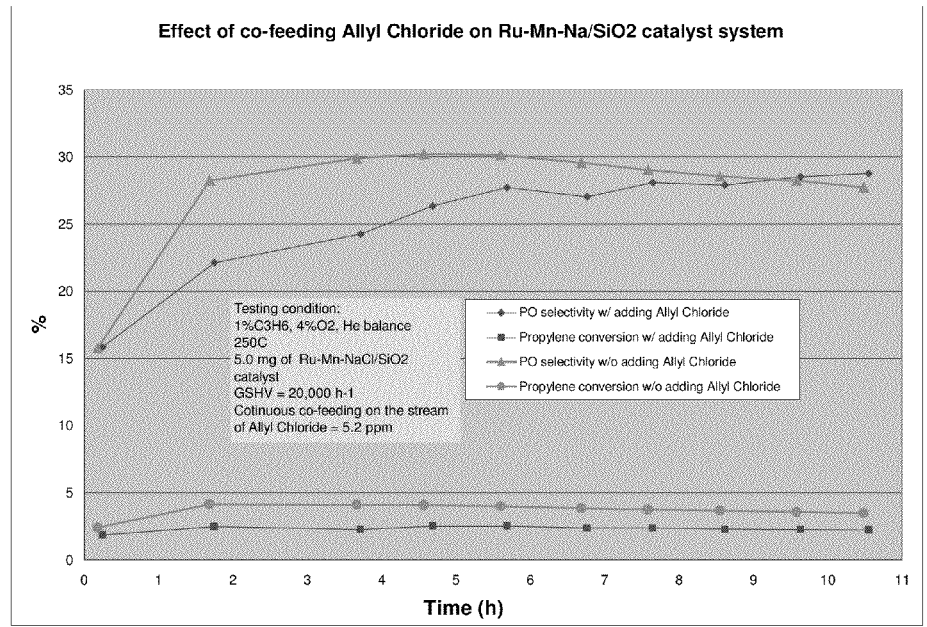
Figure 22:
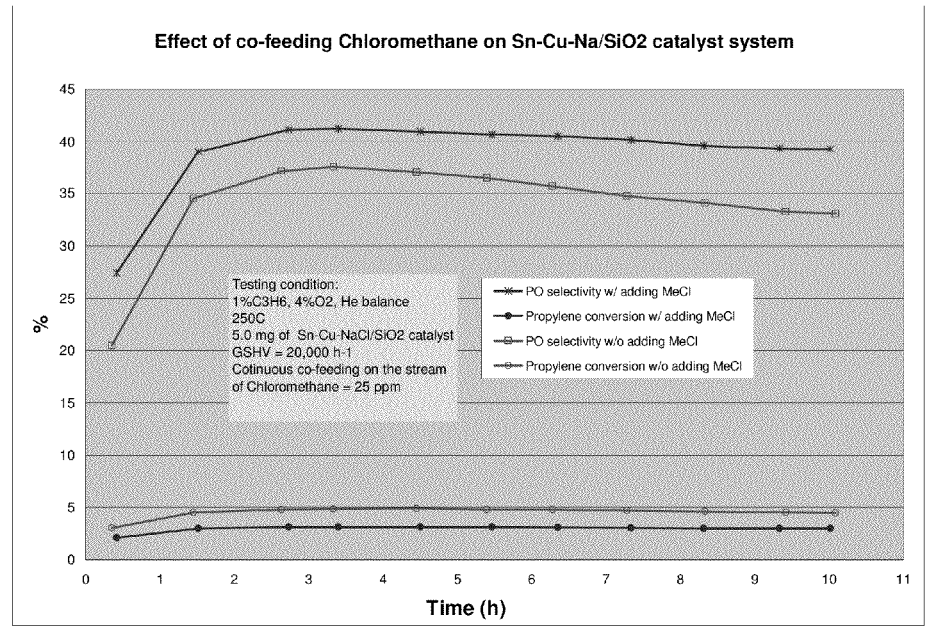
Figure 23:
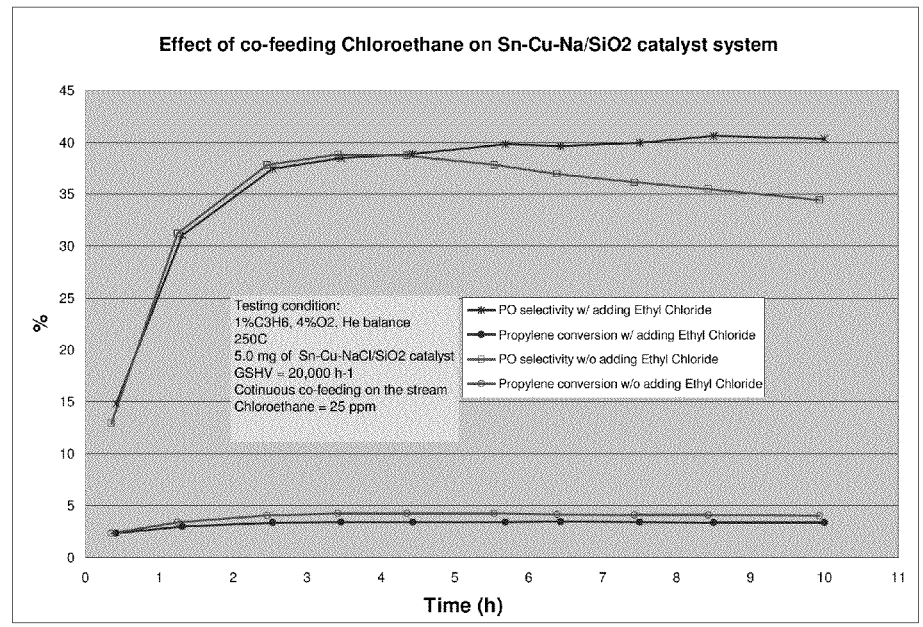
Figure 24:
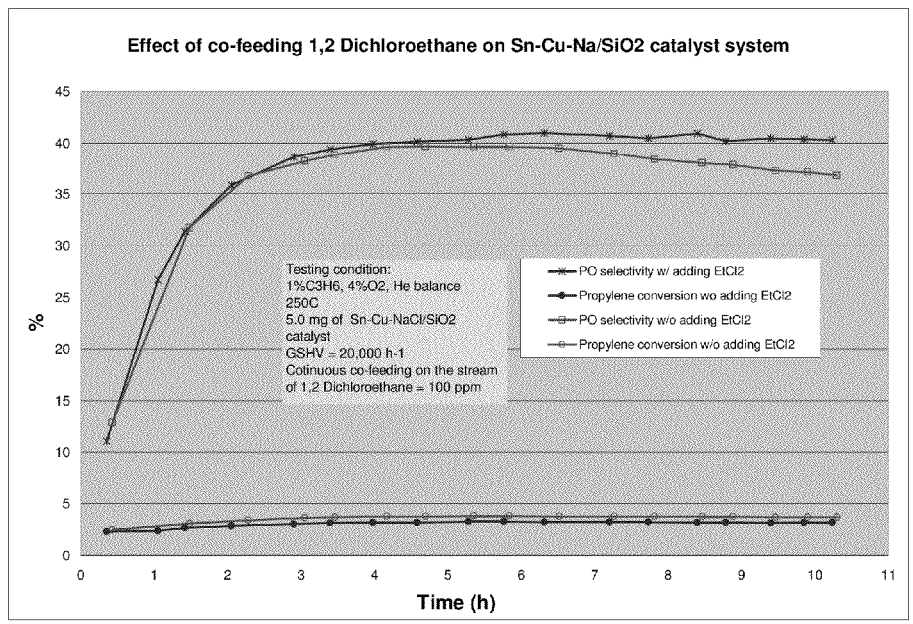
Figure 25:
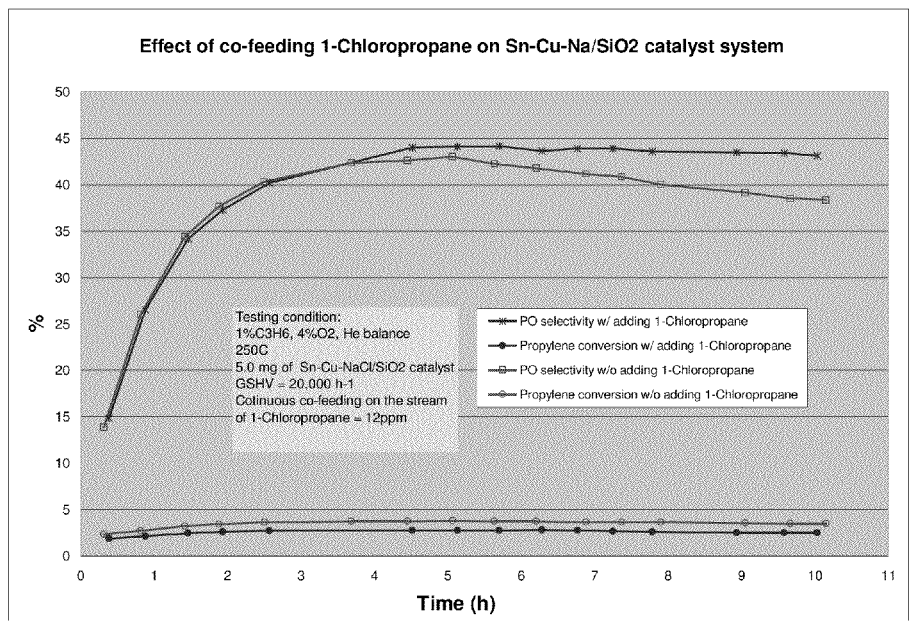
Figure 26:
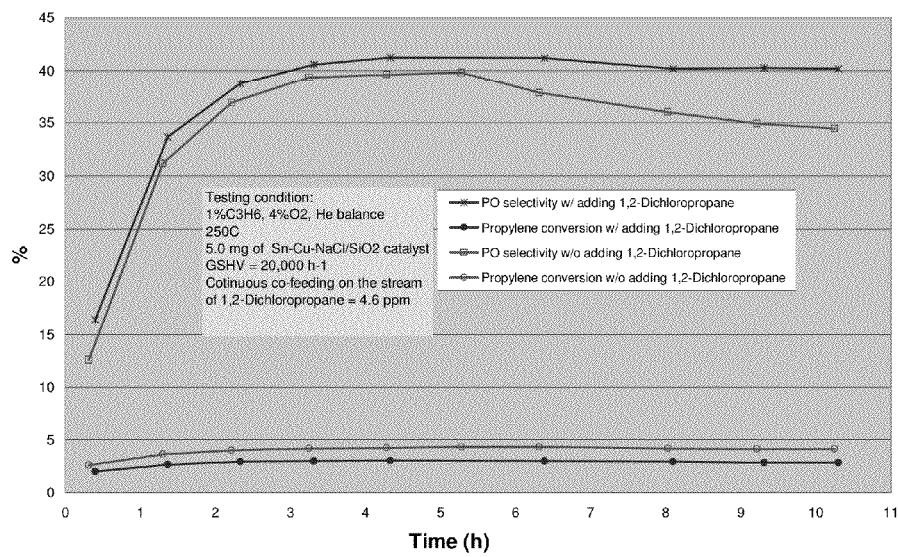
Figure 27:
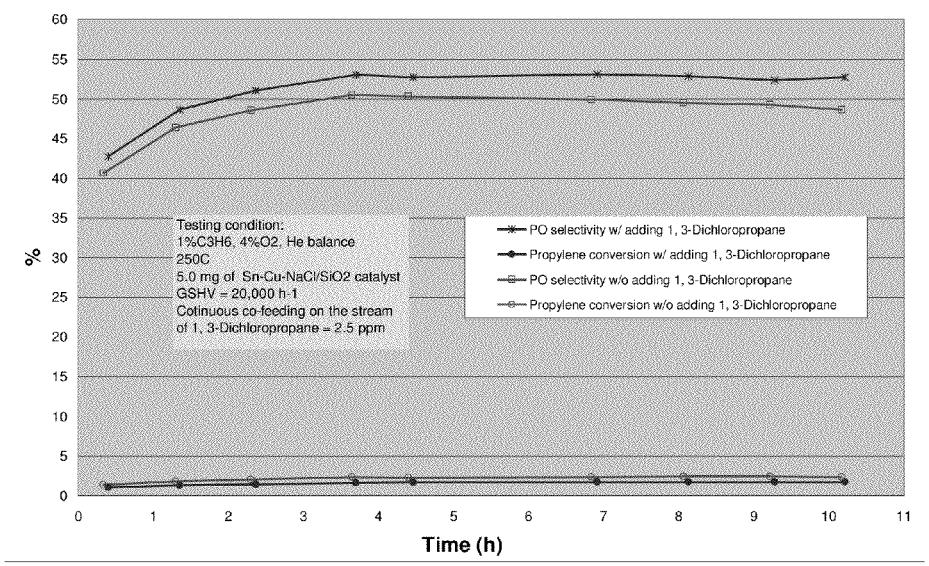
Figure 28:
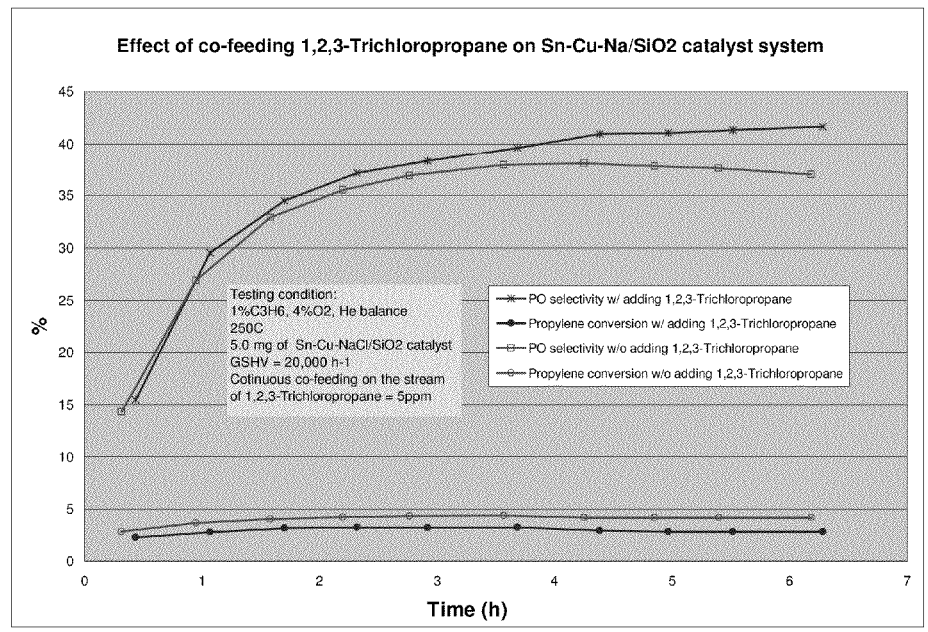
Figure 29:
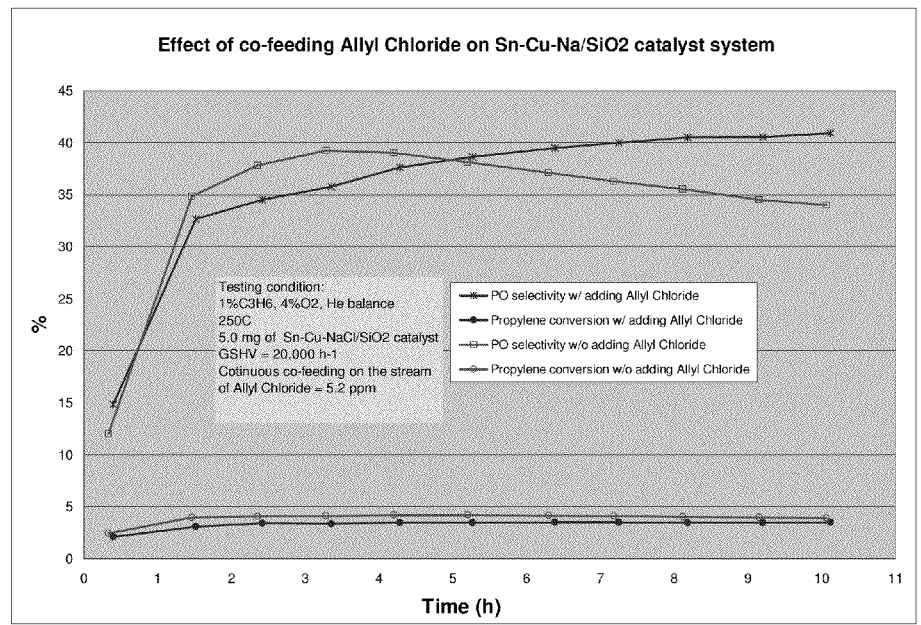
Figure 30:
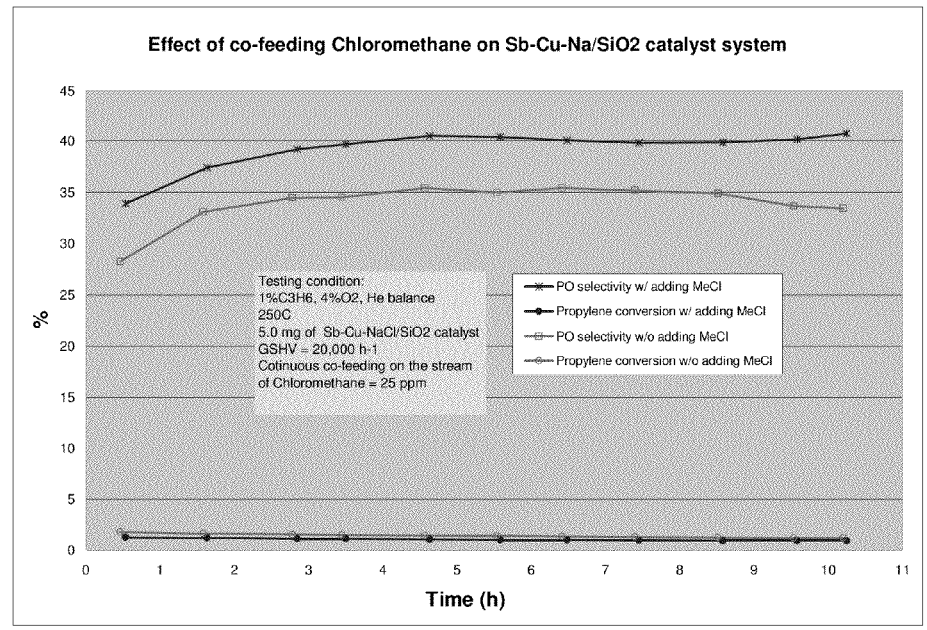
Figure 31:
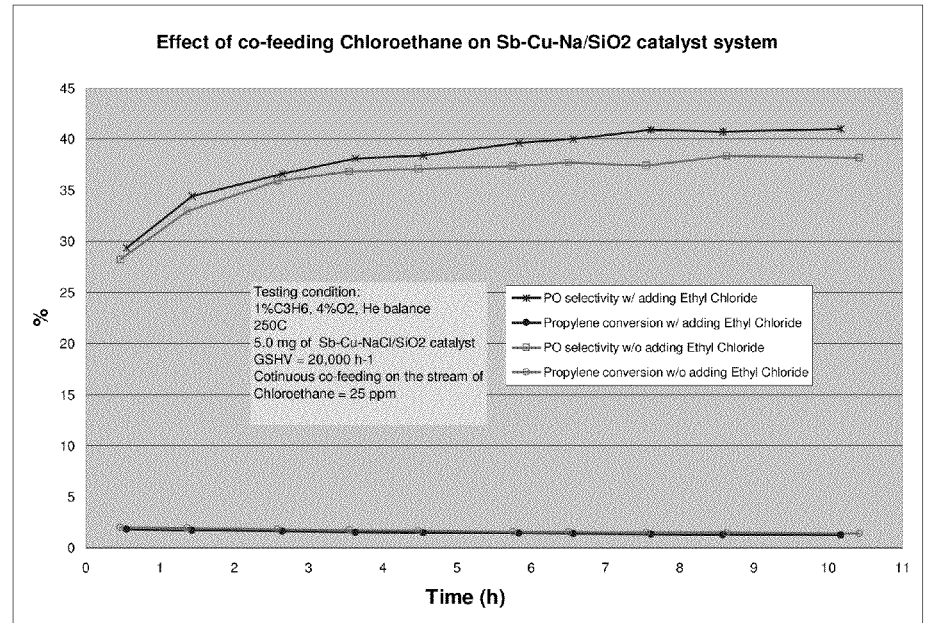
Figure 32:
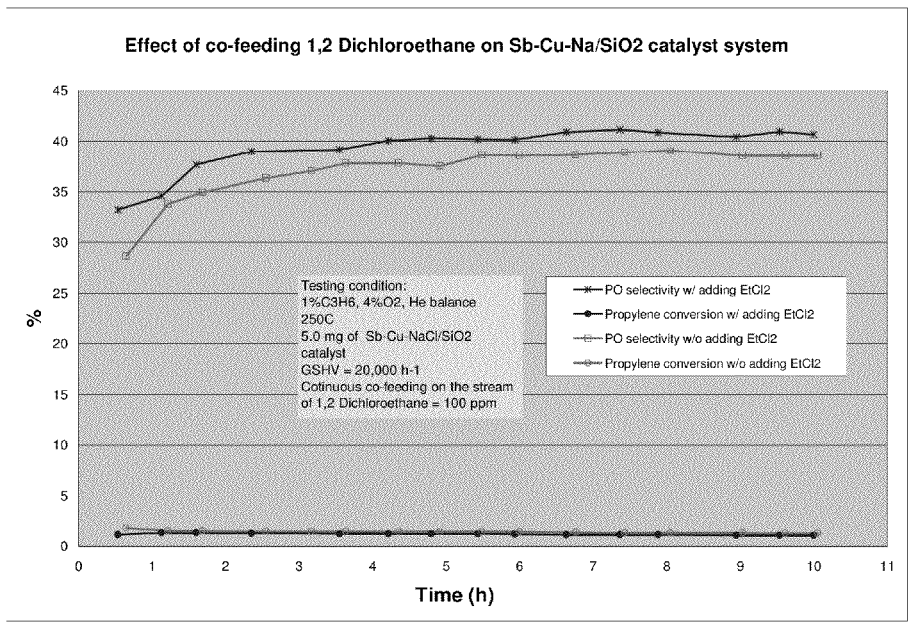
Figure 33:
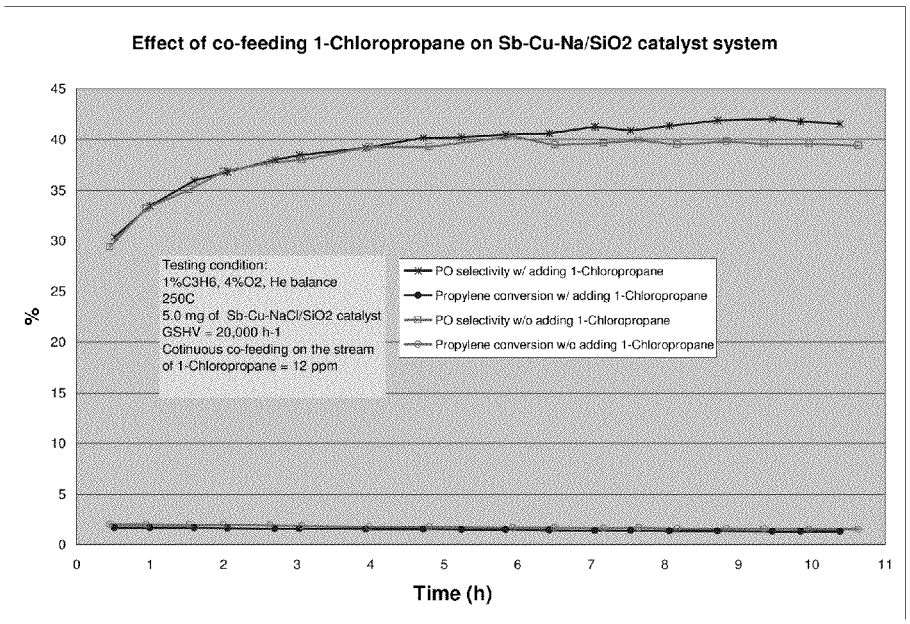
Figure 34:
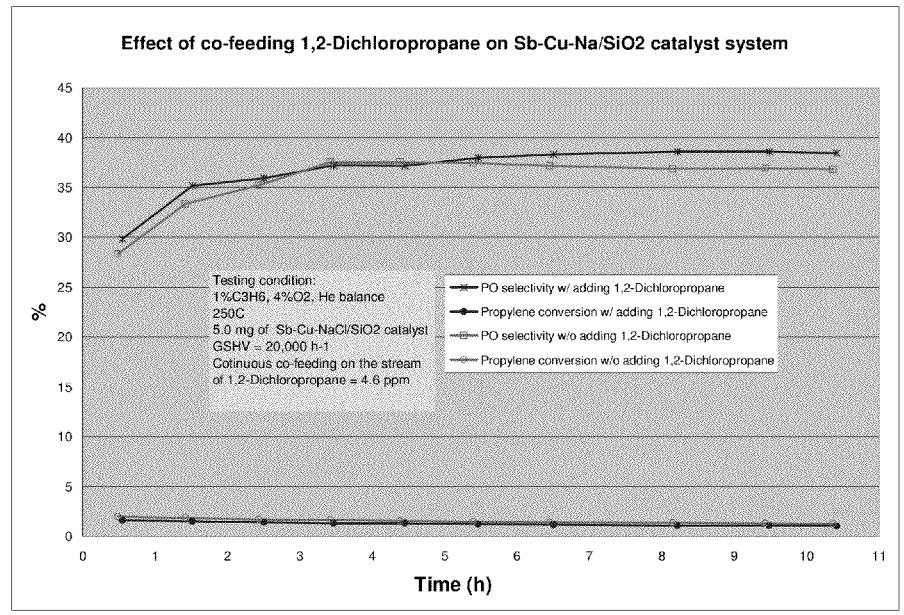
Figure 35:
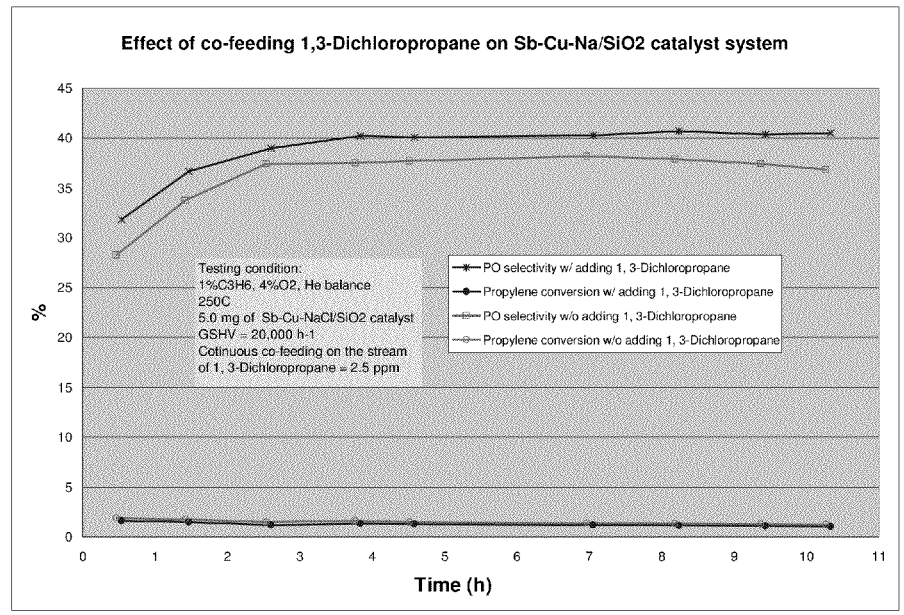
Figure 36:
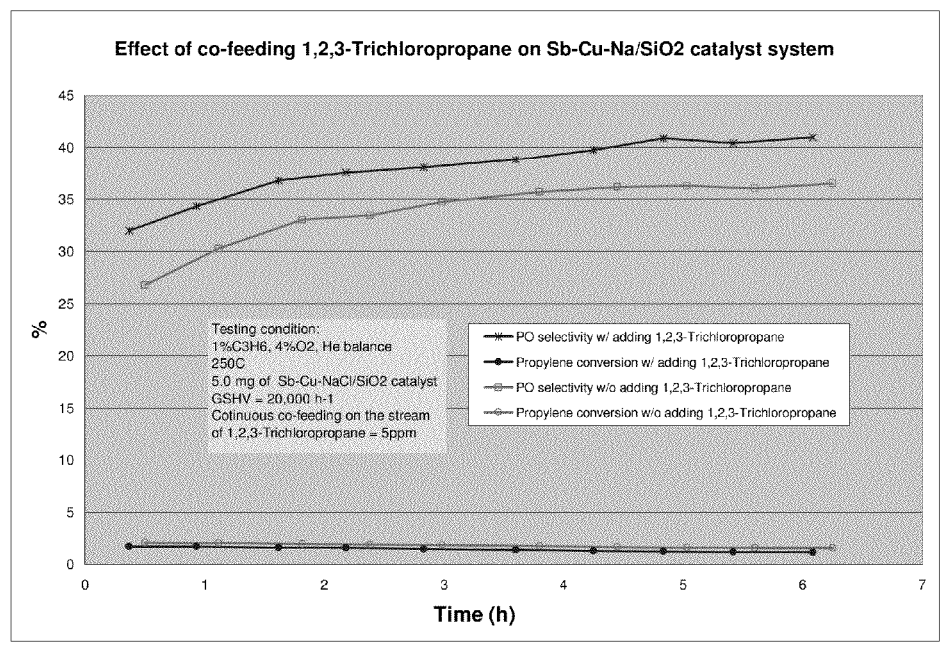
Figure 37:
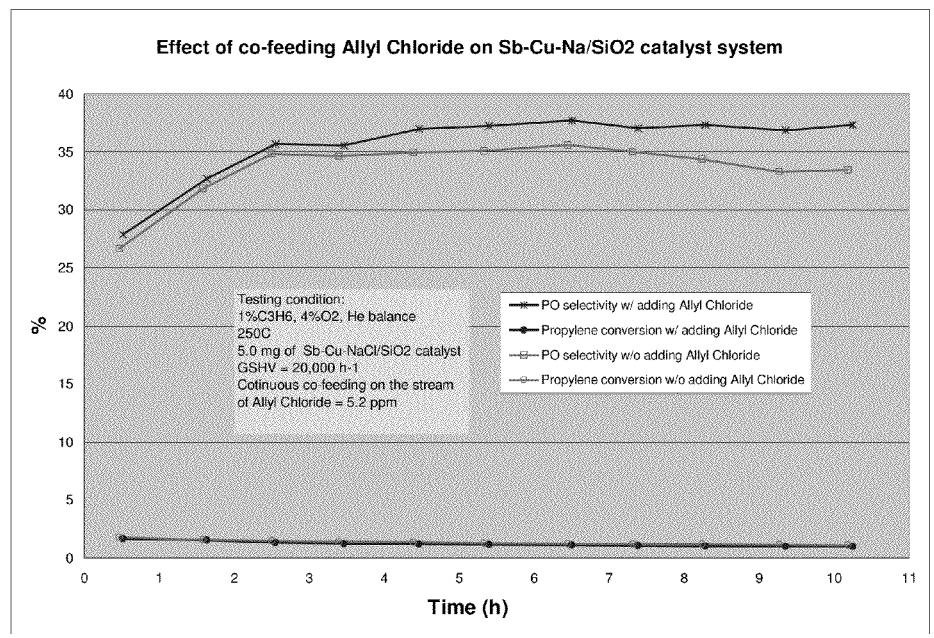
Figure 38:
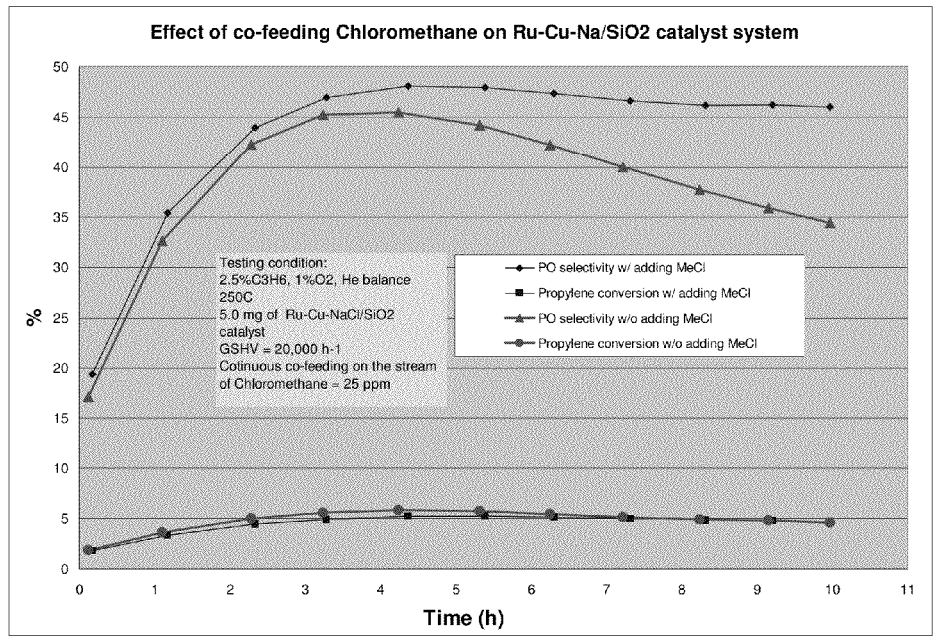
FIG. 38 to FIG. 53 are graphs showing the effects of continuously feeding 1,2-dichloroethane on Ru—Cu—NaCl/SiO$_2$ catalyst under different testing conditions, but all under propylene-rich conditions (i.e., 2.5% C$_3$H$_6$, 1% O$_2$, balance helium)
Figure 39:
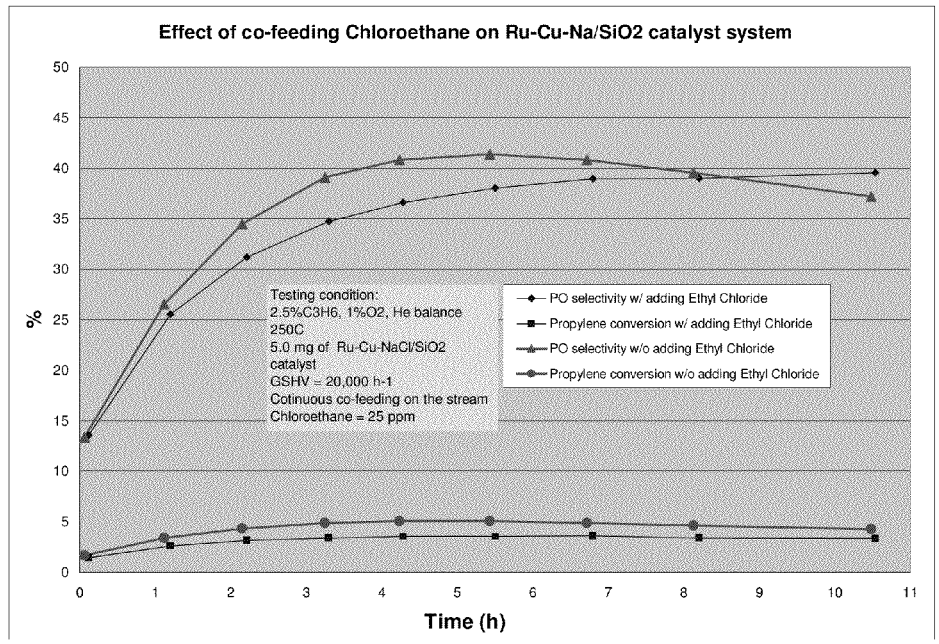
Figure 40:
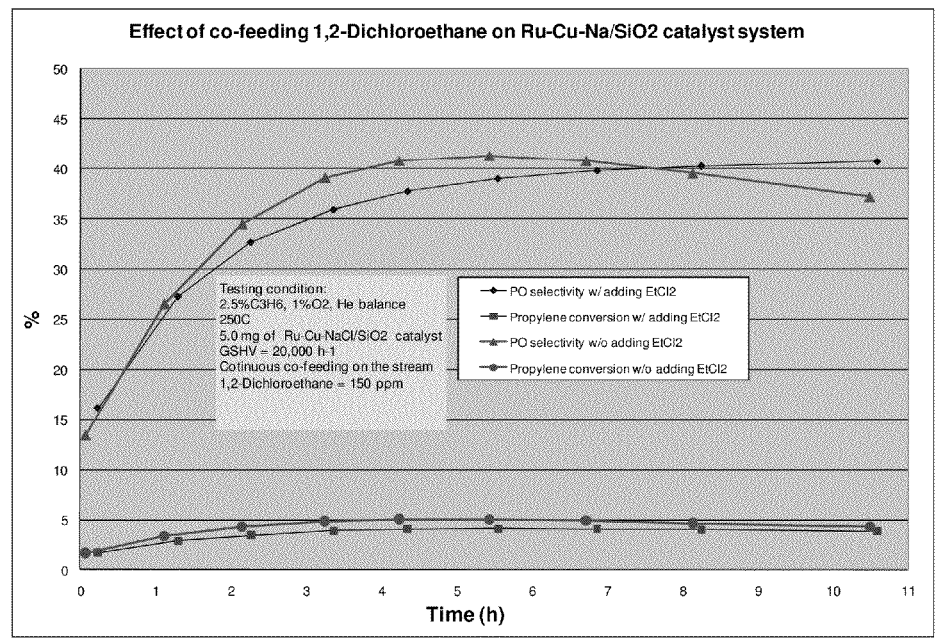
Figure 41:
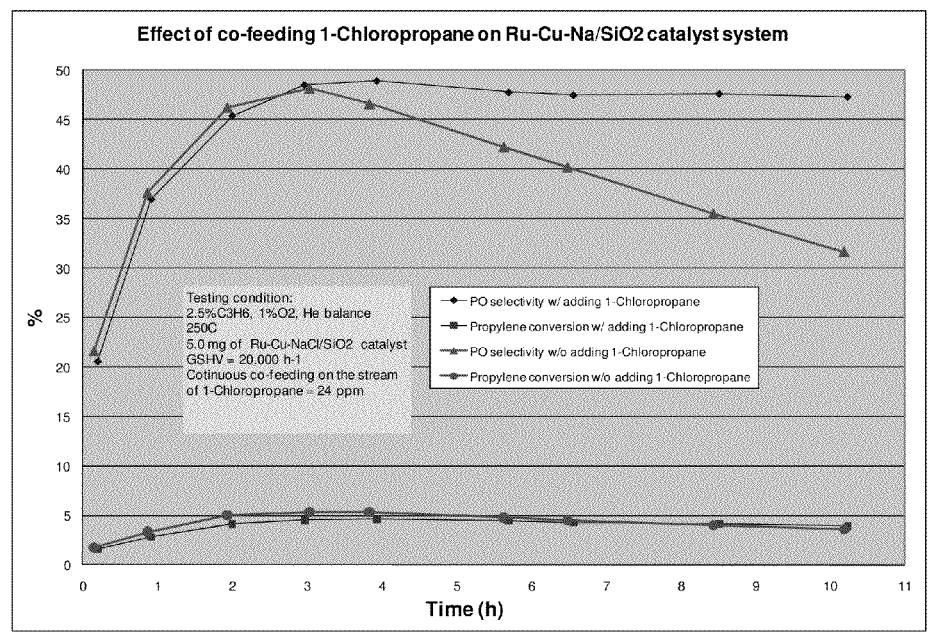
Figure 42:
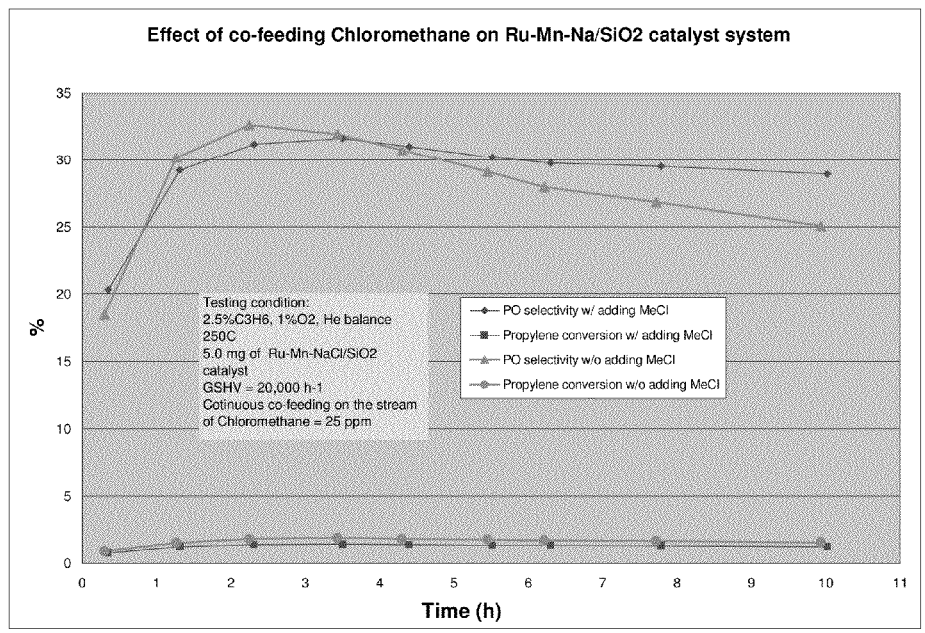
Figure 43:
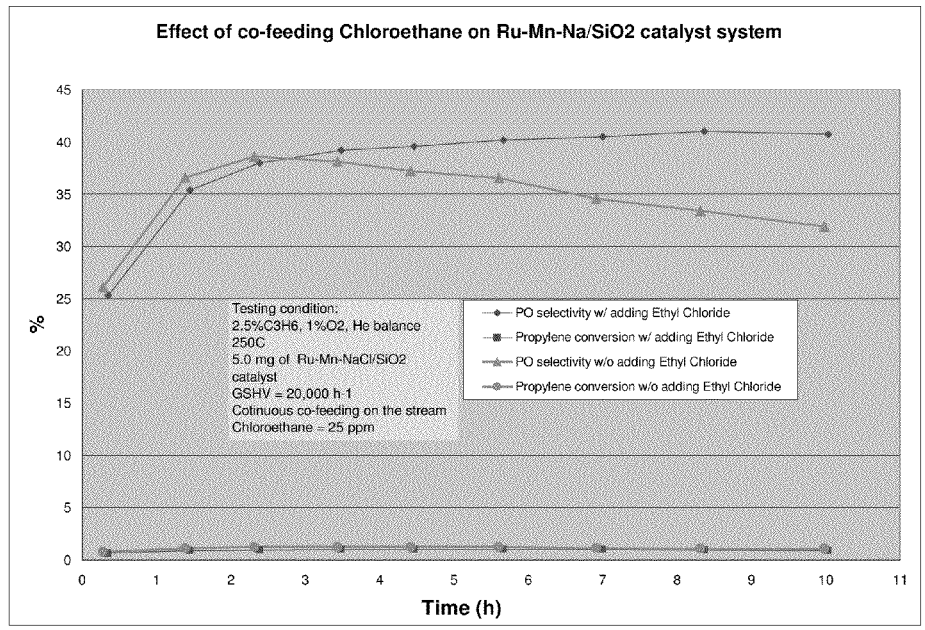
Figure 44:
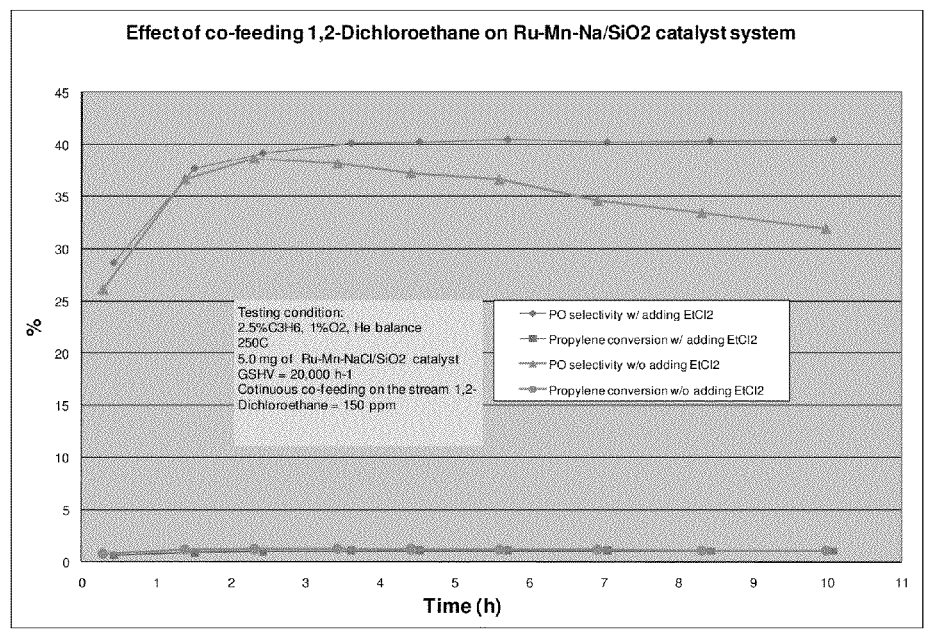
Figure 45:
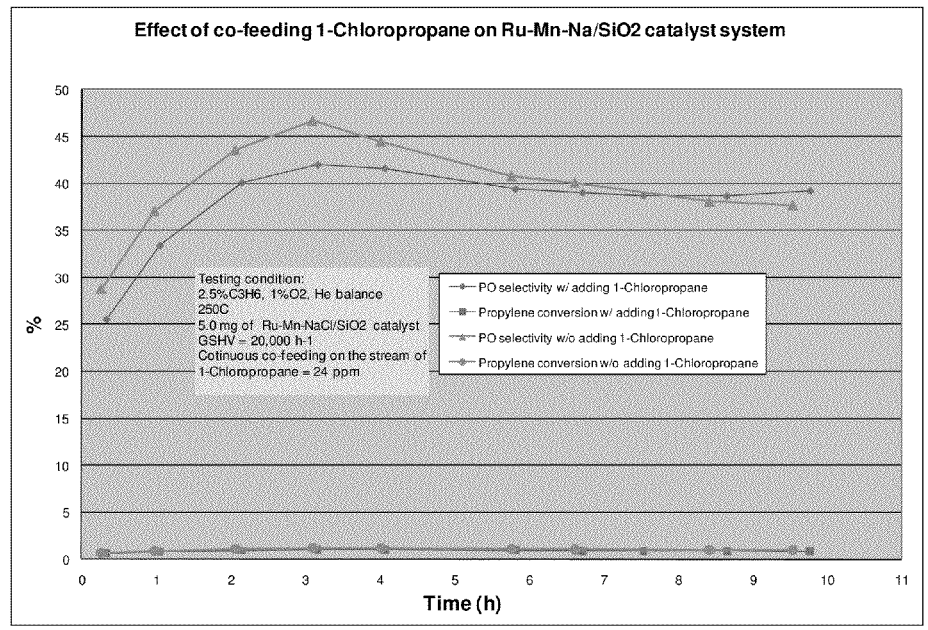
Figure 46:
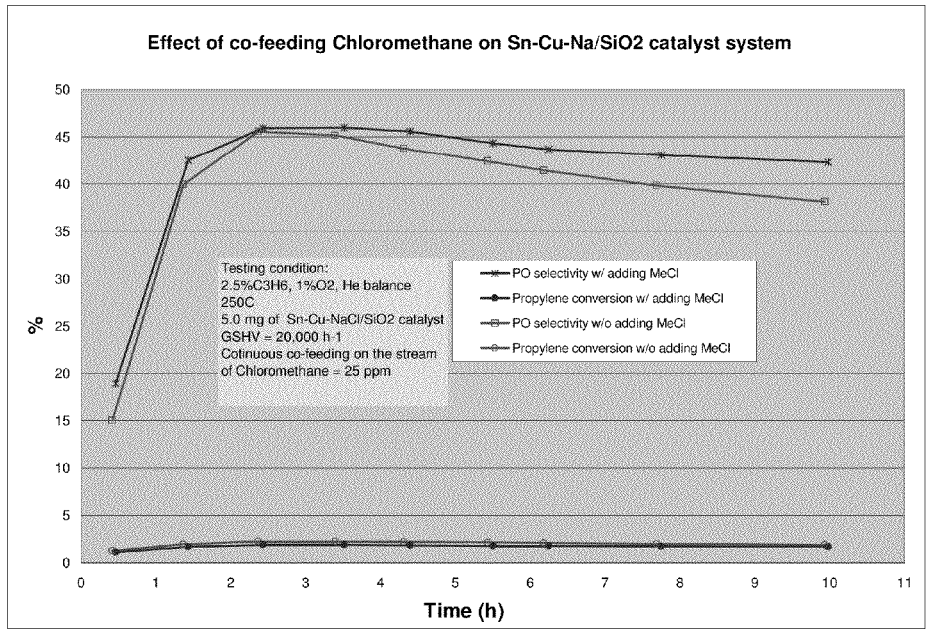
Figure 47:
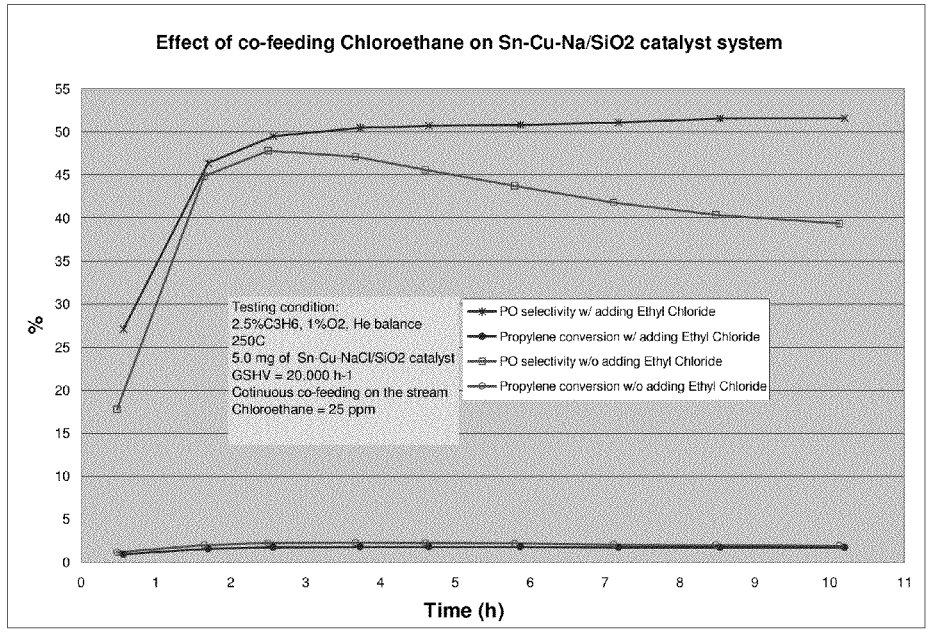
Figure 48:
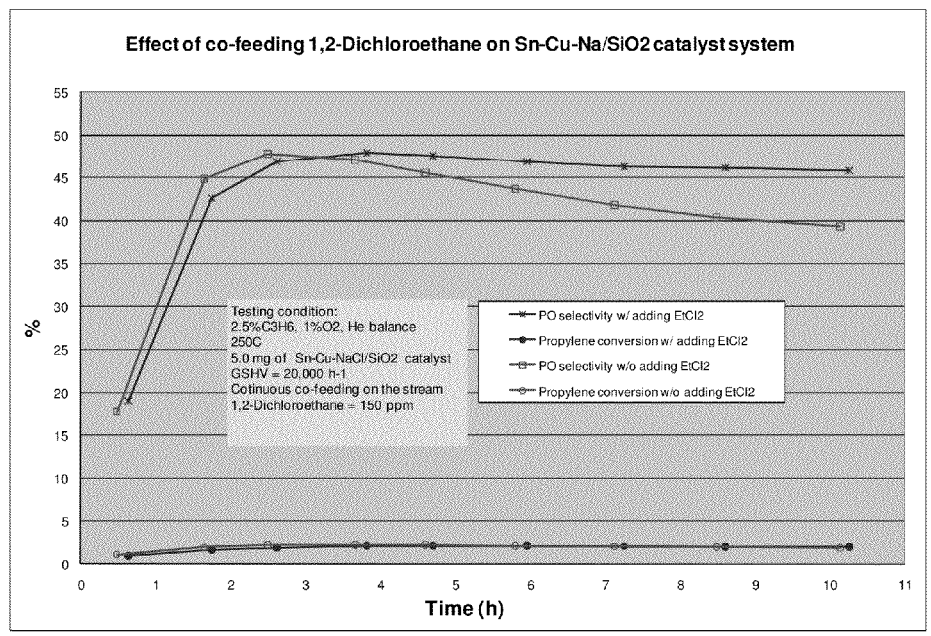
Figure 49:
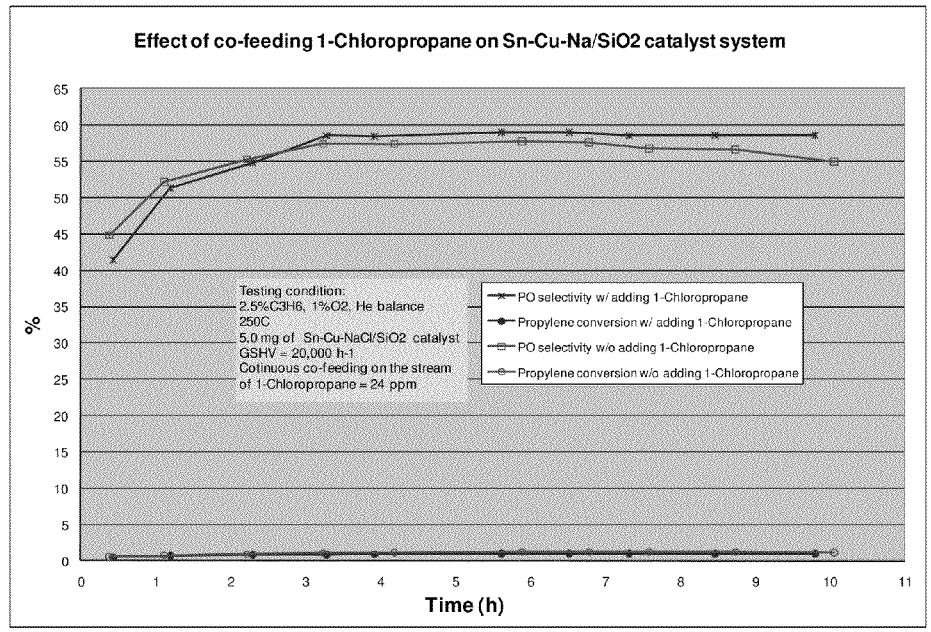
Figure 50:
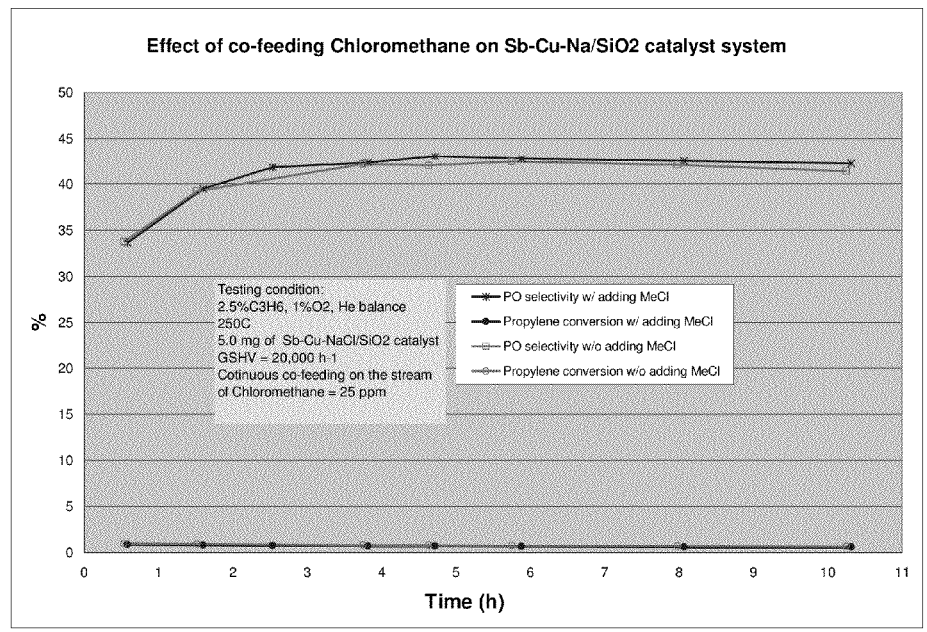
Figure 51:
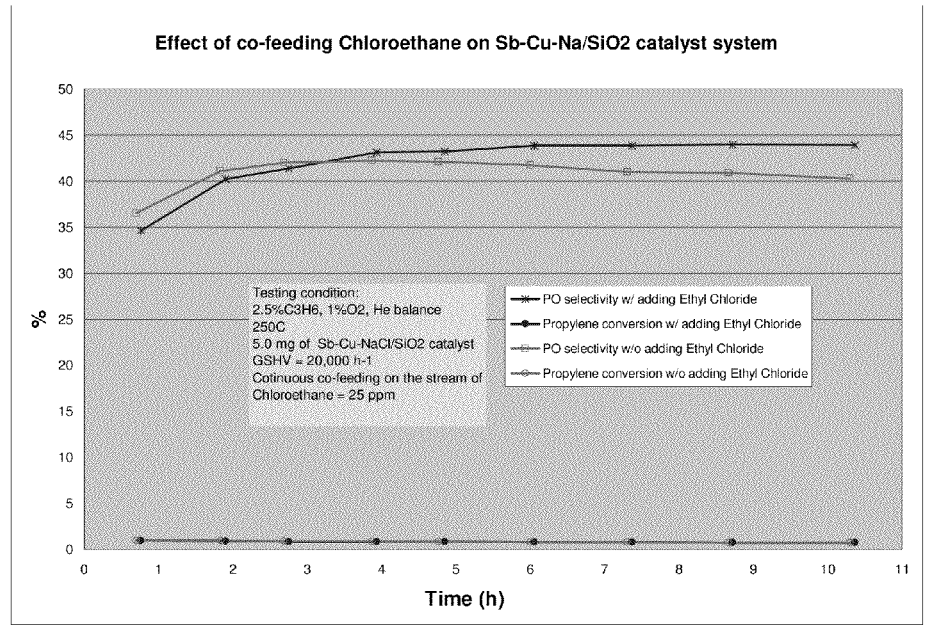
Figure 52:
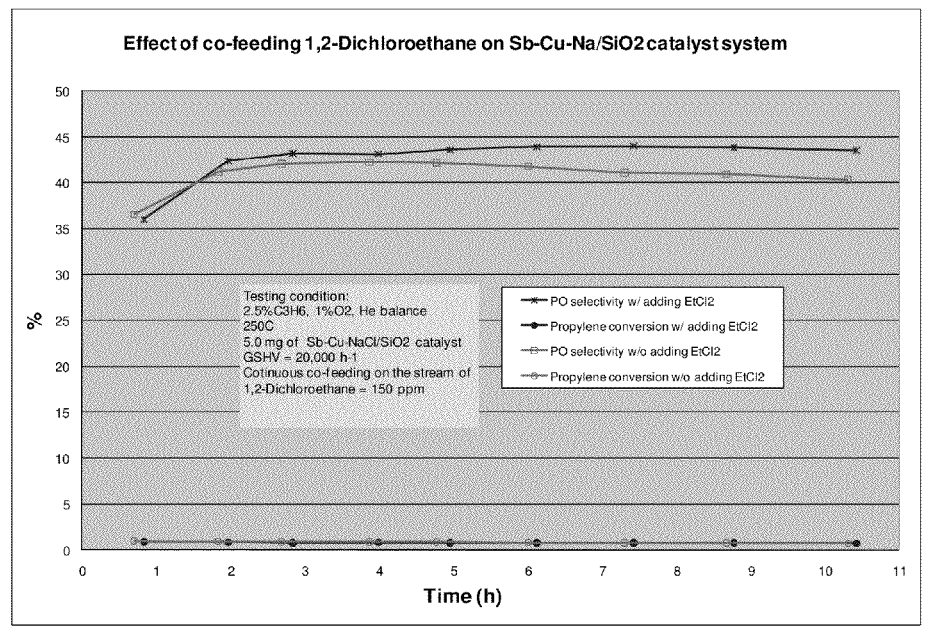
Figure 53:
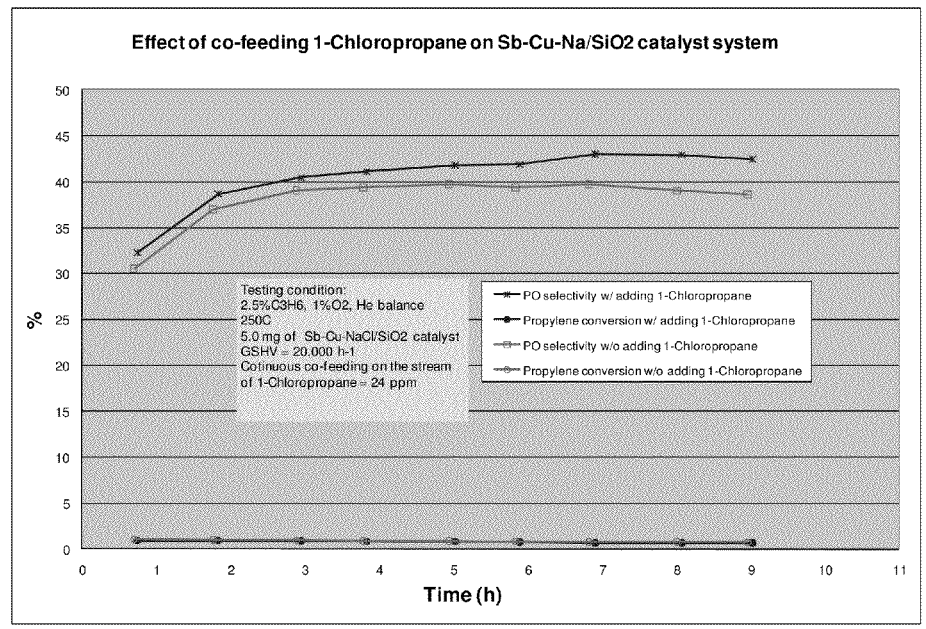

An additional experiment was carried out preparing 10.7 wt % Ru—Cu/$SiO_2$ (Ru/Cu=2/1 WR), 5 mg without a chloride source. 1,2-Dichloroethane (2,000 ppm in He, Matheson Tri-gas) was fed into the gas stream at 300 ppm. Testing conditions were as follows: 250° C., 1% of $C_3H_6$, 4% of $O_2$, and He balance, GHSV 20,000 $h^{-1}$. The results are shown in FIG. 6.

By co-feeding $EtCl_2$, PO selectivity was improved from 28% to about 45%. Propylene conversion, however, concomitantly decreased, from 5.9% to 3.0%.

Other Catalysts with Co-Feeding Organic Halides

In the following sections, we present results for the time-on-stream performances of Ru—Cu—NaCl/$SiO_2$, Ru—Mn—NaCl/$SiO_2$, Sn—Cu—NaCl/$SiO_2$ and Sb—Cu—NaCl/$SiO_2$ catalysts when the CHC additives are fed on a continuous basis. The specific experimental conditions in each case are presented as inserts in FIGS. 7-53, respectively. The results are presented first for propylene-lean conditions (i.e. 1% $C_3H_6$, 4% $O_2$, balance helium) in FIGS. 7-37, followed by the results for propylene-rich conditions (i.e. 2.5% $C_3H_6$, 1% $O_2$, balance helium) in FIGS. 38-53. As evident from these results, CHC additive generally had a beneficial effect on PO selectivities for most of the catalysts and conditions investigated. This manifested itself either as increasing PO selectivities with time or by maintaining the high PO selectivities. CHC additives had limited negative effect on propylene conversions.

The beneficial effects of CHC on PO selectivity could be due to several reasons: Geometric, electronic and gas-phase kinetic effects. The former effects include altering the adsorption energies of propylene, oxygen and PO, thereby changing the relative surface concentrations of species during the reaction thus altering the reaction mechanism. Since Cl also diffuses below the surface, it may also alter the electrical properties of the catalysts that way.

Since activity generally decreases in the presence of CHCs, at least in some catalysts, one can also view chlorinated additives as being mild "poisons". That is, chlorine and chlorinated compounds may be adsorbing on the catalyst surface and alter the reaction mechanism, but they may be more effective in blocking the reaction paths leading to $CO_2$ formation than PO formation. This selective poisoning would then be expressed by the observed increases in PO selectivities while the overall rates are reduced.

Finally, chlorine and chlorinated compounds may inhibit gas phase combustion reactions by reducing the concentrations of reactive free radicals such as $HO_2$, O and OH, thereby reducing the deep oxidation of PO and $C_3H_6$ to $CO_2$. The inhibition of combustion reactions by chlorinated compounds is well known. Consequently, this mechanism is also in harmony with the observed reduction in propylene conversions upon the introduction of CHC additives.

Ru—Cu—Na—Te/$SiO_2$ with Co-Feeding Organic Halides

Figure 54:
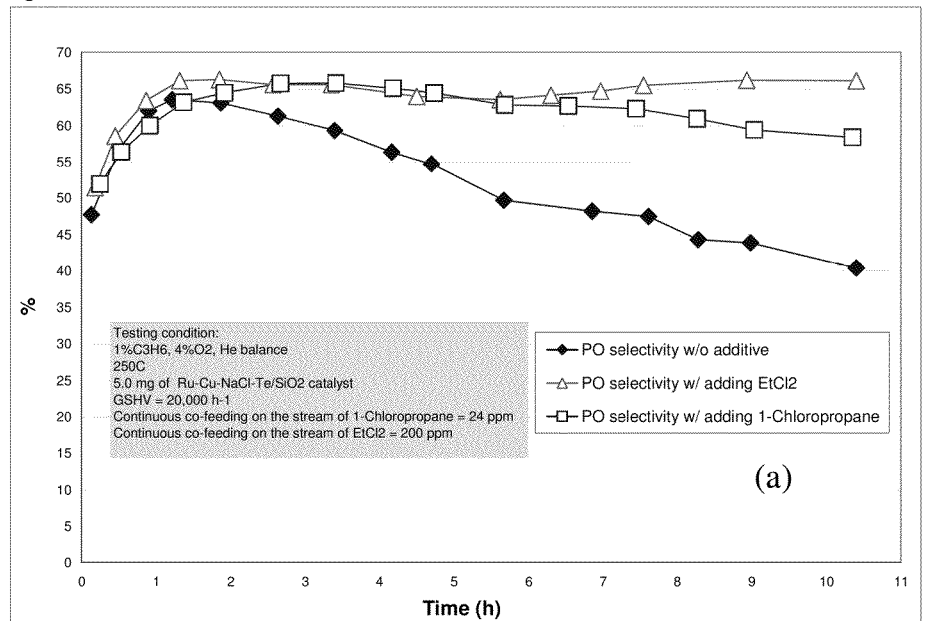
FIG. 54 is two graphs showing catalyltic performances (i.e., (a) PO selectivity, (b) propylene conversion) of Ru—Cu—Na—Te (0.5/1/1.4/0.1)/SiO$_2$, 5 mg with or without continuously co-feeding 1-chloropropane an 1,2-dichloroethane, under propylene-lean conditions (i.e., 1% C$_3$H$_6$, 4% O$_2$, balance helium), under different conditions; and, FIG. 55 is two graphs showing catalyltic performances (i.e., (a) PO selectivity, (b) propylene conversion) of Ru—Cu—Na—Te (0.5/1/1.4/0.1)/SiO$_2$, 5 mg with or without continuously co-feeding 1-chloropropane an 1,2-dichloroethane, under propylene-lean conditions (i.e., 1% C$_3$H$_6$, 4% O$_2$, balance helium), under propylene-rich conditions (i.e., 2.5% C$_3$H$_6$, 1% O$_2$, balance helium), under different conditions.
Figure 54:
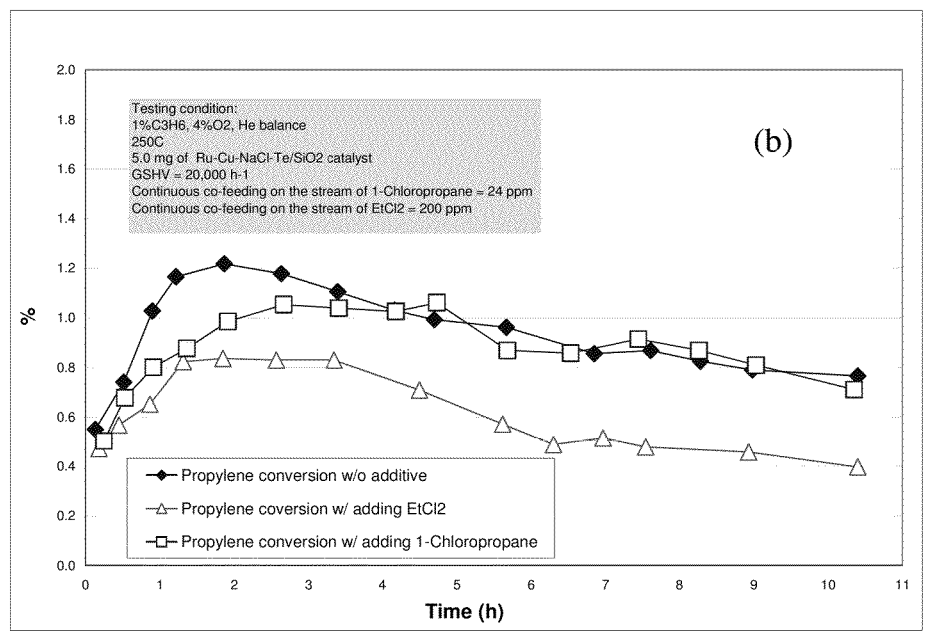
Figure 55:
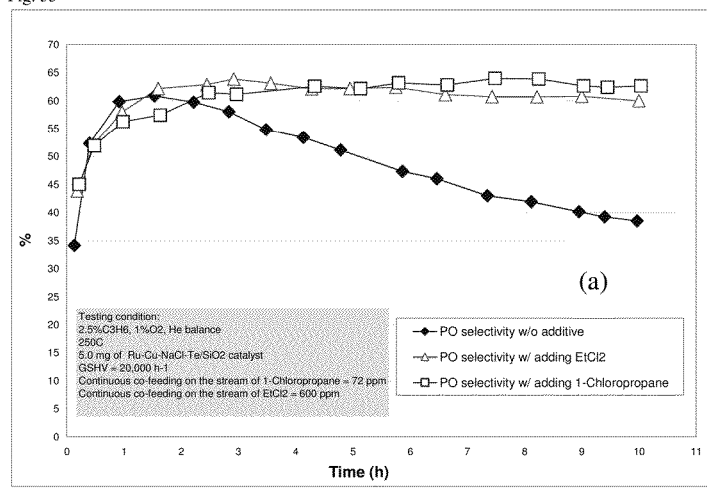
Figure 55:
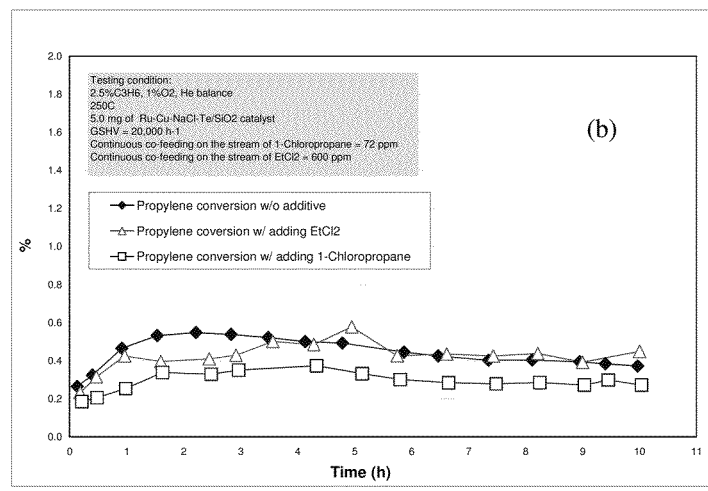

FIGS. 54 and 55 show catalyltic performances ((a) PO selectivity, (b) Propylene conversion) of Ru—Cu—Na—Te (0.5/1/1.4/0.1)/$SiO_2$, 5 mg with or without co-feeding organic halides such as 1-chloropropane or 1,2-dichloroethane. Organic halides are fed on a continuous basis. FIG. 54 presents the results for propylene-lean conditions (i.e., 1% $C_3H_6$, 4% $O_2$, balance helium, GHSV 20,000 $h^{-1}$, 250° C., Additives for Case 1: Chloropropane 24 ppm; Case 2: 1,2-Dichloroethane 200 ppm; and Case 3: no additive). FIG. 55 presents the results for propylene-rich conditions (i.e., 2.5% $C_3H_6$, 1% $O_2$, balance helium, GHSV 20,000 $h^{-1}$, 250° C., Additives for Case 1: Chloropropane 72 ppm; Case 2: 1,2-Dichloroethane 600 ppm; and Case 3: no additive).

In both conditions, PO selectivity was kept and propylene conversion was higher than without organic halides condition.

The invention claimed is:

1. A process for producing an olefin oxide, wherein the process comprises reacting an olefin with oxygen in the presence of a halogen compound additive and a catalyst comprising copper, ruthenium or both, and the reaction is performed in the gas phase wherein the halogen compound additive is a compound selected from C1-C4 halogenated alkanes and C1-C4 halogenated alkenes, and wherein the olefin and oxygen are fed in the form of gas, and a linear velocity of the gas is in the range of from 0.0001 m/s to 500 m/s.

2. The process according to claim 1, wherein the catalyst comprises a copper oxide, a ruthenium oxide or both.

3. The process according to claim 1, wherein the catalyst comprises a copper oxide and a ruthenium oxide.

4. The process according to claim 1, wherein the catalyst further comprises an alkaline metal or alkaline earth metal component.

5. The process according to claim 1, wherein the catalyst further comprises a component deriving from one selected from the group consisting of P, S, B, Mn, Ge, Tl, In, Ir, La, Ce, Bi, Re, Cr, Fe, Mo, W, Se, Sb, V, Ni, Co, Sn, Nb, Os, lanthanoid, and Te.

6. The process according to claim 5, wherein the component is a tellurium component.

7. The process according to claim 1, wherein copper, ruthenium or both are supported on a support.

8. The process according to claim 7, wherein the support is a porous support.

9. The process according to claim 1, wherein the amount of the halogen compound additive is 0.1 to 1000 ppm of entire reaction gas.

10. The process according to claim 2, wherein the ruthenium oxide is $RuO_2$.

11. The process according to claim 3, wherein the ruthenium oxide is $RuO_2$.

* * * * *